(12) United States Patent
Lathangue

(10) Patent No.: US 8,841,274 B2
(45) Date of Patent: Sep. 23, 2014

(54) PROTEIN ARGININE N-METHYLTRANSFERASE-5 METHOD OF CANCER TREATMENT

(76) Inventor: Nicholas Lathangue, Oxford (GB)

( * ) Notice: Subject to any disclaimer, the term of this patent is extended or adjusted under 35 U.S.C. 154(b) by 0 days.

(21) Appl. No.: 13/518,200

(22) PCT Filed: Dec. 20, 2010

(86) PCT No.: PCT/GB2010/052163
§ 371 (c)(1),
(2), (4) Date: Jun. 21, 2012

(87) PCT Pub. No.: WO2011/077133
PCT Pub. Date: Jun. 30, 2011

(65) Prior Publication Data
US 2013/0011497 A1   Jan. 10, 2013

(30) Foreign Application Priority Data

Dec. 22, 2009   (GB) .................................. 0922332.2

(51) Int. Cl.
*C12N 15/11* (2006.01)
*C07K 14/47* (2006.01)
*C12N 15/113* (2010.01)
*C07K 16/18* (2006.01)
*C07K 16/44* (2006.01)
*G01N 33/574* (2006.01)

(52) U.S. Cl.
CPC ........ *C07K 14/4705* (2013.01); *C12N 15/1135* (2013.01); *C12N 15/113* (2013.01); *C07K 16/18* (2013.01); *C07K 16/44* (2013.01); *C07K 2317/34* (2013.01); *C12N 15/1137* (2013.01); *C12N 2310/14* (2013.01); *G01N 33/574* (2013.01); *G01N 2800/56* (2013.01)
USPC .................................................... 514/44 A

(58) Field of Classification Search
None
See application file for complete search history.

(56) References Cited

U.S. PATENT DOCUMENTS

2004/0180002 A1 * 9/2004 Young et al. ................. 424/1.49
2006/0239990 A1   10/2006 Nabel et al.

FOREIGN PATENT DOCUMENTS

| CN | 1908187 | * | 2/2007 | ............. A61K 48/00 |
| WO | 9524223 A1 | | 9/1995 | |
| WO | 2004045543 A2 | | 6/2004 | |
| WO | 2007129091 A1 | | 11/2007 | |

OTHER PUBLICATIONS

Gura (Science, 1997, 278:1041-1042).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Van Noort and Amor (International Rev. of Cytology, 1998, vol. 178, Cell Biology of Autoimmune Diseases, pp. 127-206).*
Cheng et al. (J Biol Chem 279:23892-23899, 2004).*
Database WPI, Abstract Accession No. 2007-477636, Week 200747, Feb. 7, 2007, Thomson Scientific, London, GB; XP002628639 & CN 1908187A, Beijing Childrens Hospital, 1 page.
Jansson, M. et al., "Arginine Methylation Regulates the p53 Response," Nature Cell Biology, vol. 10, No. 12, Dec. 2008, pp. 1431-1439, XP002628641 & XP002633457 Supplementary Information, 19 pages, © 2008 Macmillan Publishers Limited.
Scoumanne, A. et al., "PRMT5 is Required for Cell-Cycle Progression and p53 Tumor Suppressor Function," Nucleic Acids Research, vol. 37, No. 15, Aug. 2009, pp. 4965-4976, XP00262860, © 2009 The Author(s).
Wang, L. et al., "Protein Arginine Methyltransferase 5 Suppresses the Transcription of the RB Family of Tumor Suppressors in Leukemia and Lymphoma Cells," Molecular and Cellular Biology, vol. 28, No. 20, Oct. 2008, pp. 6262-6277, XP002628643, © 2008 American Society for Microbiology.
Pal, S. et al., "Low Levels of miR-92b/96 Induce PRMT5 Translation and H3R8/H4R3 Methylation in Mantle Cell Lymphoma," EMBO Journal, vol. 26, No. 15, Aug. 8, 2007, pp. 3558-3569, XP008133172, © 2007 European Molecular Biology Organization.
Tanaka, H. et al., "PRMT5, a Novel Trail Receptor-Binding Protein, Inhibits Trail-Induced Apoptosis via Nuclear Factor-kB Activation," Molecular Cancer Research, vol. 7, No. 4, Apr. 2009, pp. 557-569, XP002628642, © 2009 American Association for Cancer Research.
Bruns, A.F. et al., "Fibroblast Growth Factor 2 (FGF2) is a Novel Substrate for Arginine Methylation by PRMT5," Biological Chemistry, vol. 390, No. 1, Jan. 1, 2009, pp. 59-65, XP008134467, © Walter De Gruyer GMBH & Co.
Fabbrizio, E. et al., "Negative Regulation of Transcription by the Type II Arginine Methyltransferase PRMT5," EMBO Reports, vol. 3, No. 7, pp. 641-645, 2002, © 2002 European Molecular Biology Organization.
Yoshimoto, T. et al., "The Arginine Methyltransferase PRMT2 Binds RB and Regulates E2F Function," Experimental Cell Research, vol. 312, pp. 2040-2053, 2006, published by Elsevier Inc.
Frietze, S. et al., "CARM1 Regulates Estrogen-Stimulated Breast Cancer Growth Through Up-Regulation on E2F1," Cancer Research, Jan. 1, 2008, vol. 68, pp. 301-306, © American Association for Cancer Research.
GB Search Report, Appln. No. GB0922332.2, Date of search: Apr. 21, 2010, 2 pages.

* cited by examiner

*Primary Examiner* — Peter J Reddig
(74) *Attorney, Agent, or Firm* — Rothwell, Figg, Ernst & Manbeck P.C.

(57) ABSTRACT

A method for the treatment of a proliferative disease comprising providing a E2F-1 protein which is arginine-methylation defective or administering a substance which reduces the expression and/or activity of PRMT5. The invention also provides antibodies, screening methods and kits.

5 Claims, 27 Drawing Sheets

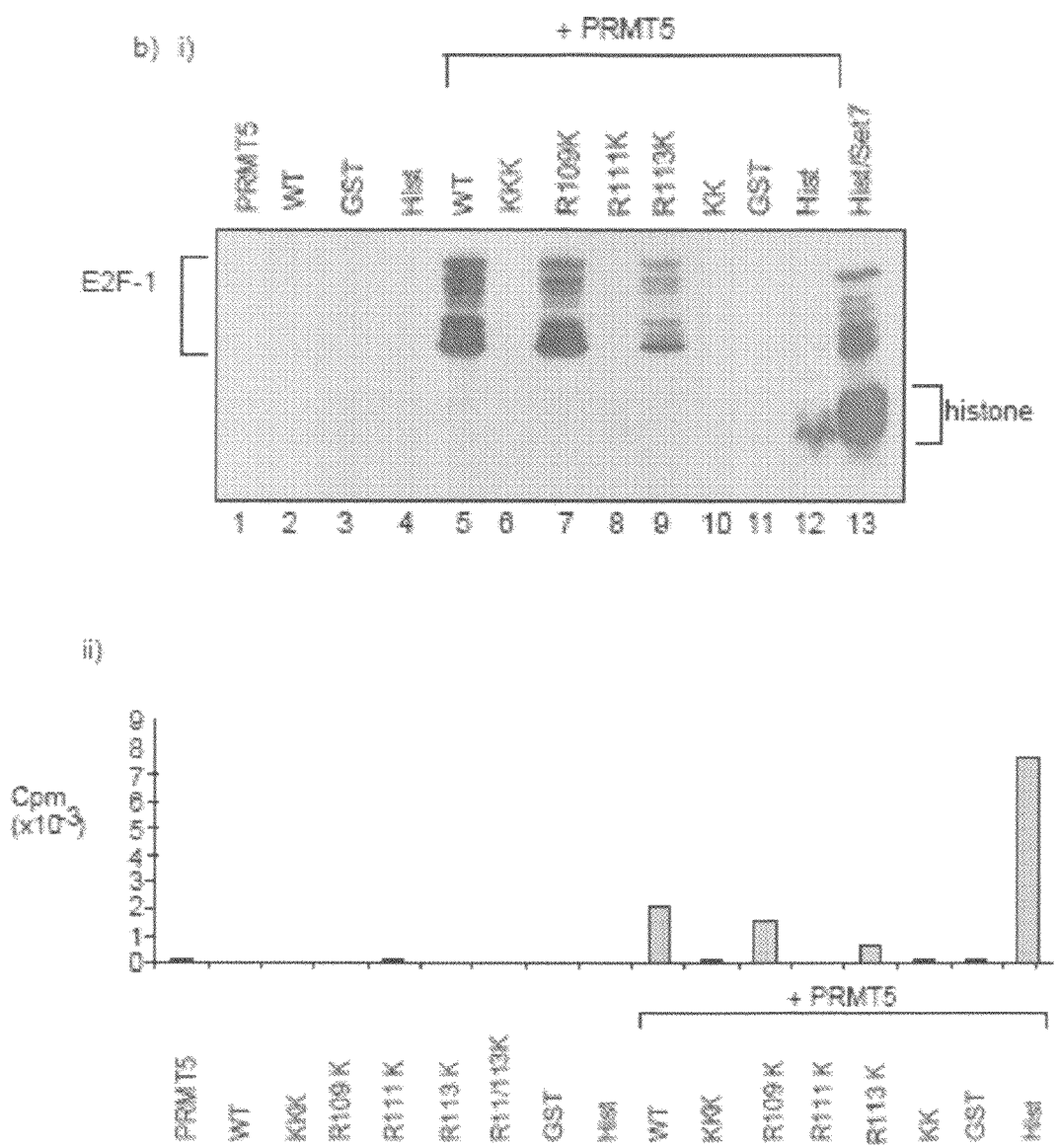

c)

d)

a)

b)

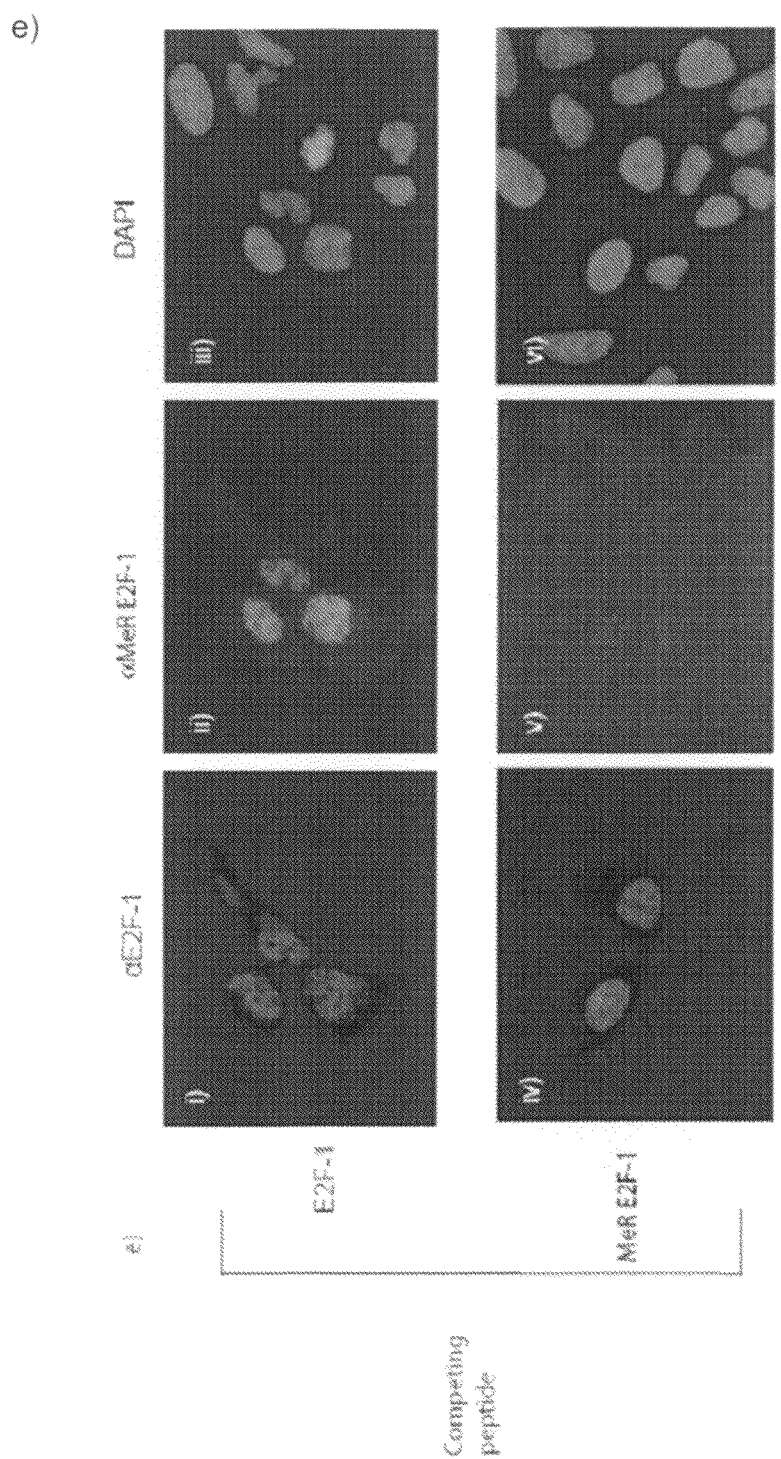

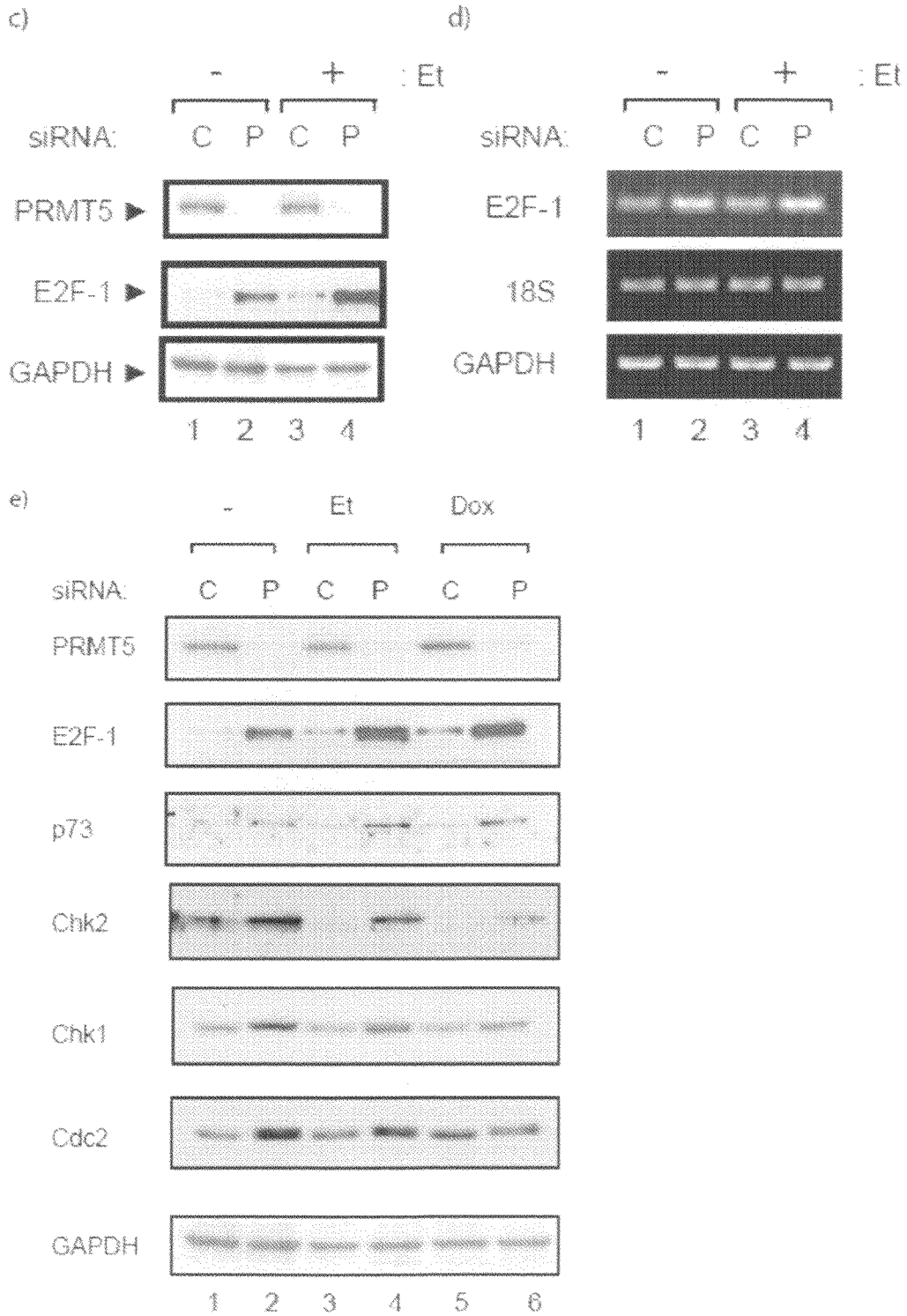

f)

h)

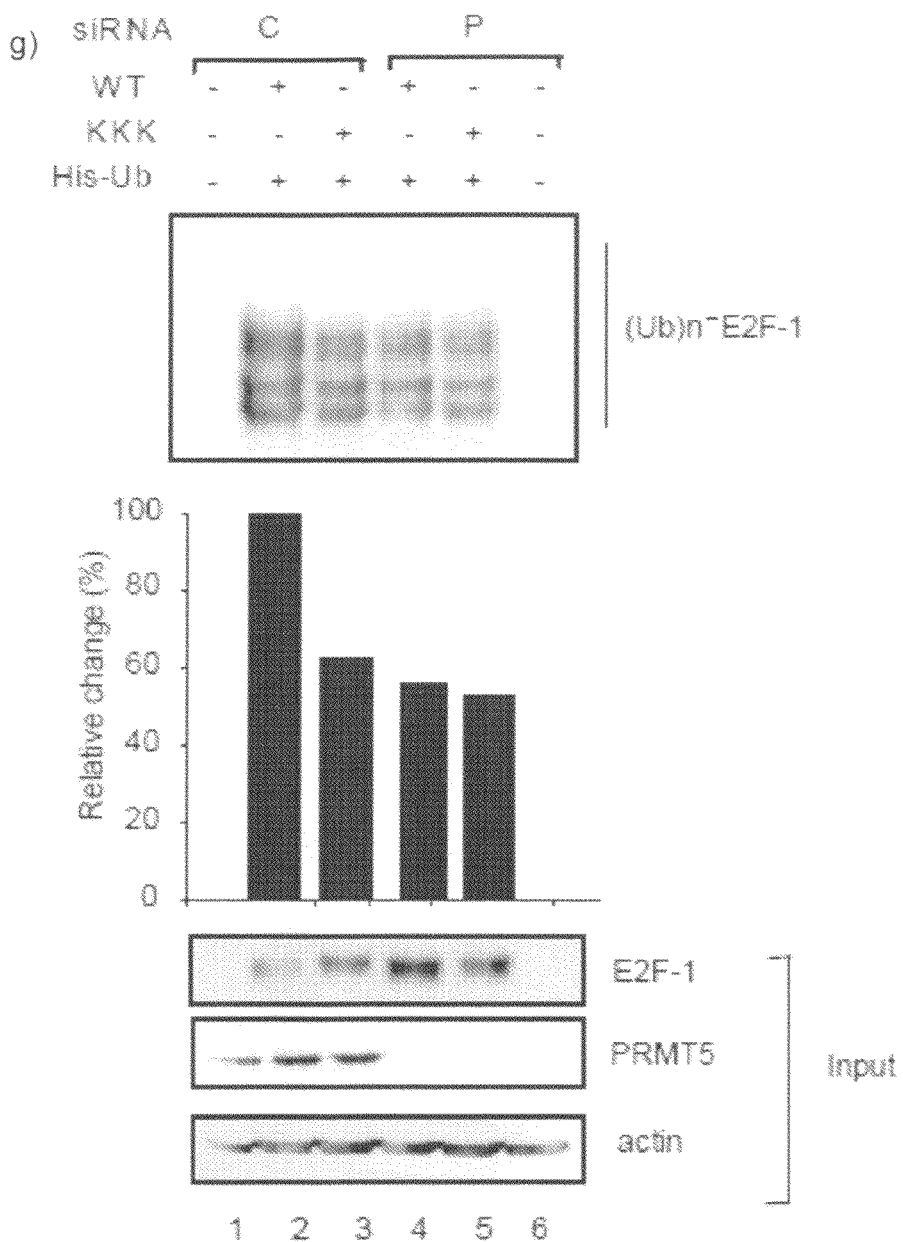

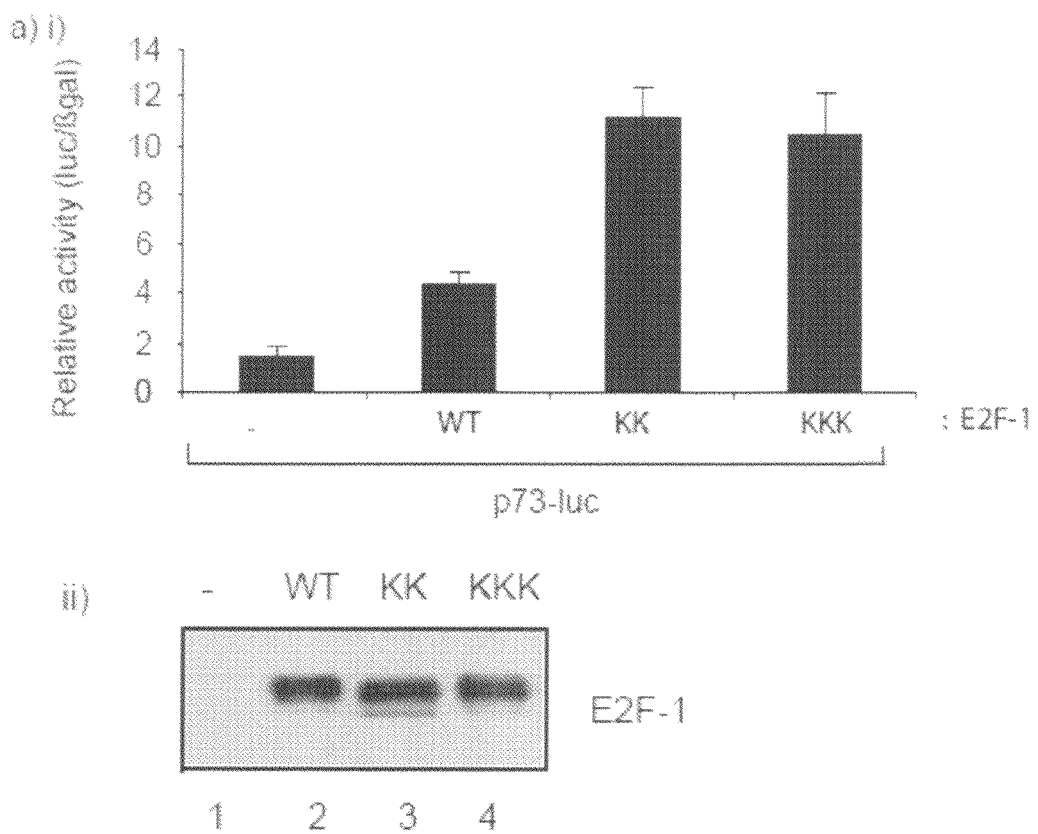

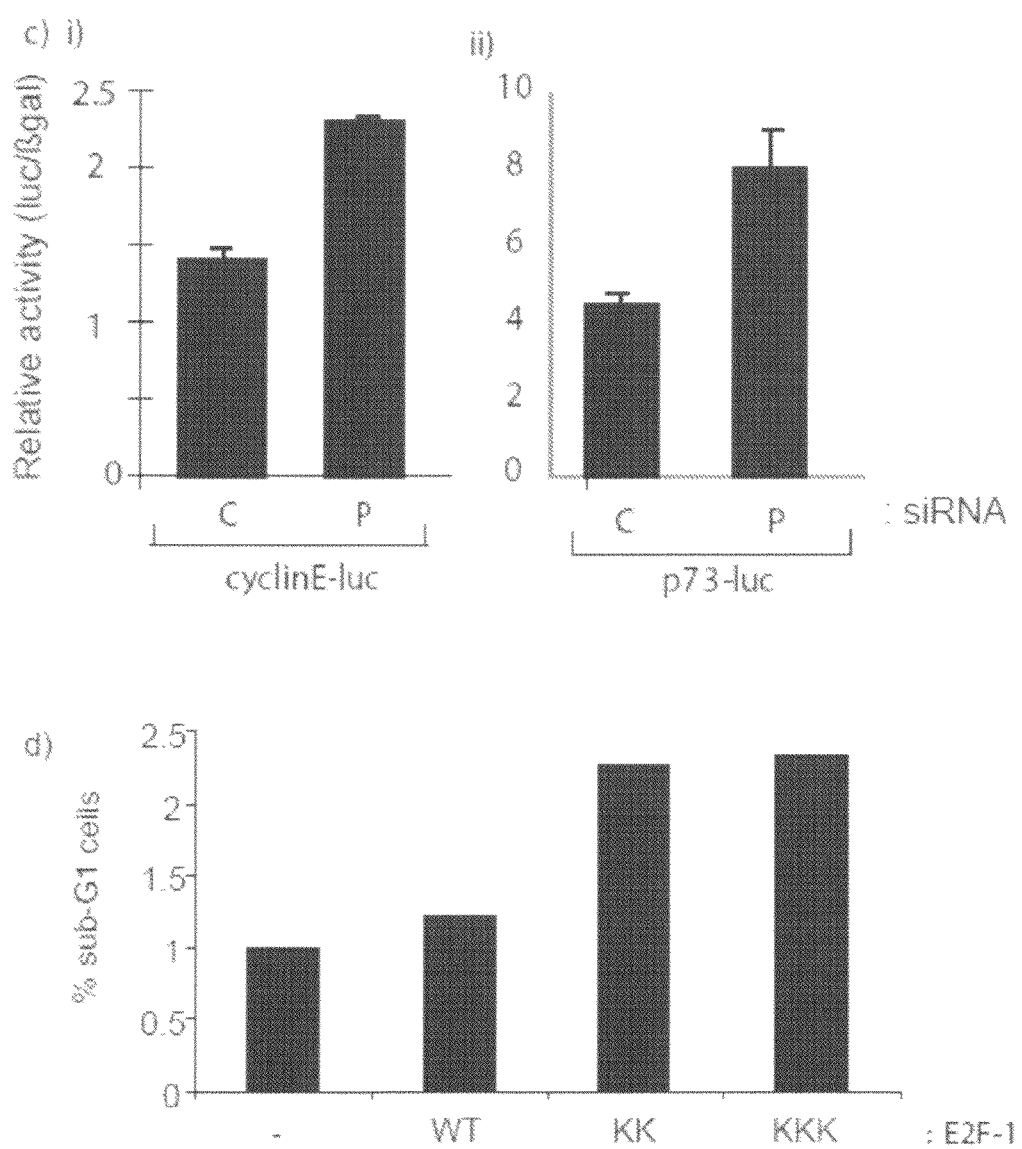

Methylation cell cycle arrest

No methylation apoptosis

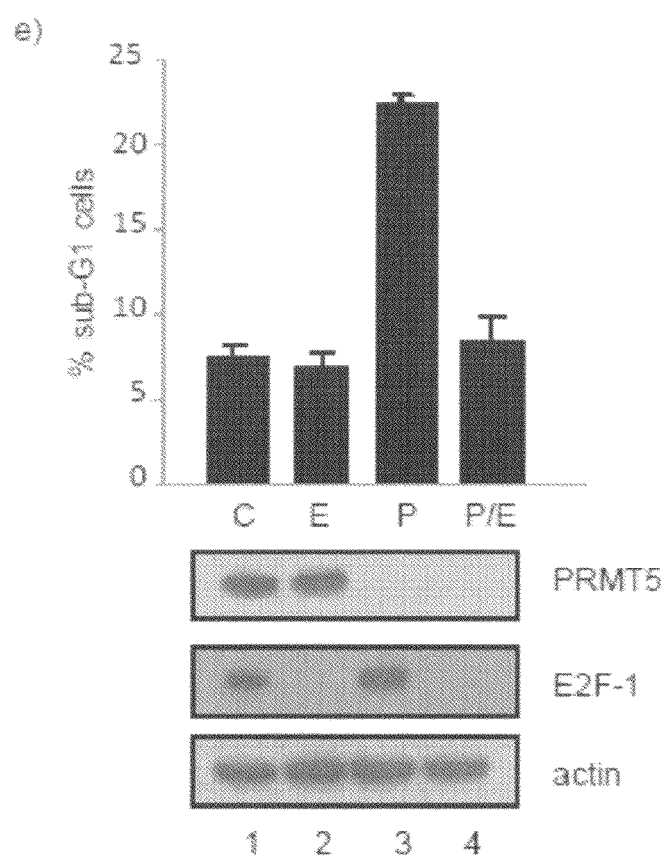

SEQUENCE LISTING

<160> NUMBER OF SEQ ID NOS: 19

<210> SEQ ID NO 1
<211> LENGTH: 19
<212> TYPE: RNA
<213> ORGANISM: Artificial
<220> FEATURE:
<223> OTHER INFORMATION: siRNA

<400> SEQUENCE: 1
ccgcuauugc accuuggaa                                                      19

<210> SEQ ID NO 2
<211> LENGTH: 19
<212> TYPE: RNA
<213> ORGANISM: Artificial
<220> FEATURE:
<223> OTHER INFORMATION: siRNA

<400> SEQUENCE: 2
caacagagau ccuaugauu                                                      19

<210> SEQ ID NO 3
<211> LENGTH: 437
<212> TYPE: PRT
<213> ORGANISM: Homo sapiens

<400> SEQUENCE: 3

Met Ala Leu Ala Gly Ala Pro Ala Gly Gly Pro Cys Ala Pro Ala Leu
1               5                   10                  15

Glu Ala Leu Leu Gly Ala Gly Ala Leu Arg Leu Leu Asp Ser Ser Gln
            20                  25                  30

Ile Val Ile Ile Ser Ala Ala Gln Asp Ala Ser Ala Pro Pro Ala Pro
        35                  40                  45

Thr Gly Pro Ala Ala Pro Ala Gly Pro Cys Asp Pro Asp Leu Leu
    50                  55                  60

Leu Phe Ala Thr Pro Gln Ala Pro Arg Pro Thr Pro Ser Ala Pro Arg
65                  70                  75                  80

Pro Ala Leu Gly Arg Pro Pro Val Lys Arg Arg Leu Asp Leu Glu Thr
                85                  90                  95

Asp His Gln Tyr Leu Ala Glu Ser Ser Gly Pro Ala Arg Gly Arg Gly
            100                 105                 110

Arg His Pro Gly Lys Gly Val Lys Ser Pro Gly Glu Lys Ser Arg Tyr
        115                 120                 125

Glu Thr Ser Leu Asn Leu Thr Thr Lys Arg Phe Leu Glu Leu Leu Ser
    130                 135                 140

His Ser Ala Asp Gly Val Val Asp Leu Asn Trp Ala Ala Glu Val Leu
145                 150                 155                 160

Lys Val Gln Lys Arg Arg Ile Tyr Asp Ile Thr Asn Val Leu Glu Gly
                165                 170                 175

Ile Gln Leu Ile Ala Lys Lys Ser Lys Asn His Ile Gln Trp Leu Gly
            180                 185                 190

Ser His Thr Thr Val Gly Val Gly Gly Arg Leu Glu Gly Leu Thr Gln
        195                 200                 205

Asp Leu Arg Gln Leu Gln Glu Ser Glu Gln Gln Leu Asp His Leu Met
    210                 215                 220

Asn Ile Cys Thr Thr Gln Leu Arg Leu Leu Ser Glu Asp Thr Asp Ser
225                 230                 235                 240

-continued

```
Gln Arg Leu Ala Tyr Val Thr Cys Gln Asp Leu Arg Ser Ile Ala Asp
                245                 250                 255

Pro Ala Glu Gln Met Val Met Val Ile Lys Ala Pro Pro Glu Thr Gln
            260                 265                 270

Leu Gln Ala Val Asp Ser Ser Glu Asn Phe Gln Ile Ser Leu Lys Ser
        275                 280                 285

Lys Gln Gly Pro Ile Asp Val Phe Leu Cys Pro Glu Glu Thr Val Gly
    290                 295                 300

Gly Ile Ser Pro Gly Lys Thr Pro Ser Gln Glu Val Thr Ser Glu Glu
305                 310                 315                 320

Glu Asn Arg Ala Thr Asp Ser Ala Thr Ile Val Ser Pro Pro Ser
                325                 330                 335

Ser Pro Pro Ser Ser Leu Thr Thr Asp Pro Ser Gln Ser Leu Leu Ser
            340                 345                 350

Leu Glu Gln Glu Pro Leu Leu Ser Arg Met Gly Ser Leu Arg Ala Pro
        355                 360                 365

Val Asp Glu Asp Arg Leu Ser Pro Leu Val Ala Ala Asp Ser Leu Leu
    370                 375                 380

Glu His Val Arg Glu Asp Phe Ser Gly Leu Leu Pro Glu Glu Phe Ile
385                 390                 395                 400

Ser Leu Ser Pro Pro His Glu Ala Leu Asp Tyr His Phe Gly Leu Glu
                405                 410                 415

Glu Gly Glu Gly Ile Arg Asp Leu Phe Asp Cys Asp Phe Gly Asp Leu
            420                 425                 430

Thr Pro Leu Asp Phe
        435

<210> SEQ ID NO 4
<211> LENGTH: 5
<212> TYPE: PRT
<213> ORGANISM: Homo sapiens

<400> SEQUENCE: 4

Arg Gly Arg Gly Arg
1               5

<210> SEQ ID NO 5
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (5)..(5)
<223> OTHER INFORMATION: METHYLATION

<400> SEQUENCE: 5

Arg Gly Arg Gly Arg
1               5

<210> SEQ ID NO 6
<211> LENGTH: 17
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: METHYLATION
<220> FEATURE:
```

```
<221> NAME/KEY: MOD_RES
<222> LOCATION: (12)..(12)
<223> OTHER INFORMATION: METHYLATION

<400> SEQUENCE: 6

Cys Glu Ser Ser Gly Pro Ala Arg Gly Arg Gly Arg His Pro Gly Lys
1               5                   10                  15

Gly

<210> SEQ ID NO 7
<211> LENGTH: 17
<212> TYPE: PRT
<213> ORGANISM: Homo sapiens

<400> SEQUENCE: 7

Cys Glu Ser Ser Gly Pro Ala Arg Gly Arg Gly Arg His Pro Gly Lys
1               5                   10                  15

Gly

<210> SEQ ID NO 8
<211> LENGTH: 32
<212> TYPE: DNA
<213> ORGANISM: Artificial
<220> FEATURE:
<223> OTHER INFORMATION: primer

<400> SEQUENCE: 8
gagcagtggg ccagctaaag gcagaggccg cc                              32

<210> SEQ ID NO 9
<211> LENGTH: 32
<212> TYPE: DNA
<213> ORGANISM: Artificial
<220> FEATURE:
<223> OTHER INFORMATION: primer

<400> SEQUENCE: 9
ggcggcctct gcctttagct ggcccactgc tc                              32

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
agctcggggc aaaggccgcc atc                                        23

<210> SEQ ID NO 11
<211> LENGTH: 23
<212> TYPE: DNA
<213> ORGANISM: Artificial
<220> FEATURE:
<223> OTHER INFORMATION: primer

<400> SEQUENCE: 11
gggcagaggc aaacatccag gaa                                        23

<210> SEQ ID NO 12
<211> LENGTH: 45
<212> TYPE: DNA
<213> ORGANISM: Artificial
<220> FEATURE:
<223> OTHER INFORMATION: primer
```

```
<400> SEQUENCE: 12
agtgggccag ctcggggcaa aggcaaacat ccaggaaaag gtgtg                    45

<210> SEQ ID NO 13
<211> LENGTH: 50
<212> TYPE: DNA
<213> ORGANISM: Artificial
<220> FEATURE:
<223> OTHER INFORMATION: primer

<400> SEQUENCE: 13
agagcagtgg gccagctaag ggcaagggca agcatccagg aaaaggtgtg               50

<210> SEQ ID NO 14
<211> LENGTH: 5
<212> TYPE: PRT
<213> ORGANISM: Homo sapiens

<400> SEQUENCE: 14

Arg Gly Arg Gly Arg
1               5

<210> SEQ ID NO 15
<211> LENGTH: 5
<212> TYPE: PRT
<213> ORGANISM: Artificial
<220> FEATURE:
<223> OTHER INFORMATION: R109K motif

<400> SEQUENCE: 15

Lys Gly Arg Gly Arg
1               5

<210> SEQ ID NO 16
<211> LENGTH: 5
<212> TYPE: PRT
<213> ORGANISM: Artificial
<220> FEATURE:
<223> OTHER INFORMATION: R111K motif

<400> SEQUENCE: 16

Arg Gly Lys Gly Arg
1               5

<210> SEQ ID NO 17
<211> LENGTH: 5
<212> TYPE: PRT
<213> ORGANISM: Artificial
<220> FEATURE:
<223> OTHER INFORMATION: R113K motif

<400> SEQUENCE: 17

Arg Gly Arg Gly Lys
1               5

<210> SEQ ID NO 18
<211> LENGTH: 5
<212> TYPE: PRT
<213> ORGANISM: Artificial
<220> FEATURE:
<223> OTHER INFORMATION: R111/113K motif (KK)

<400> SEQUENCE: 18

Arg Gly Lys Gly Lys
1               5
```

```
<210> SEQ ID NO 19
<211> LENGTH: 5
<212> TYPE: PRT
<213> ORGANISM: Artificial
<220> FEATURE:
<223> OTHER INFORMATION: R109/111/113K motif (KKK)

<400> SEQUENCE: 19

Lys Gly Lys Gly Lys
1               5
```

PROTEIN ARGININE N-METHYLTRANSFERASE-5 METHOD OF CANCER TREATMENT

CROSS-REFERENCE TO RELATED APPLICATIONS

The present application is a national stage filing under 35 U.S.C. §371 of PCT/GB2010/052163, filed on 20 Dec. 2010 which in turn claims priority to United Kingdom Patent Application No. GB 0922332.2, filed on 22 Dec. 2009. The disclosures of each of the above applications are hereby incorporated by reference in their entireties into the present application.

SEQUENCE SUBMISSION

A Sequence Listing in electronic format was filed with the application on 21 Jun. 2012. The Sequence Listing is entitled SequenceListing 177.txt, created on 21 Dec. 2009 and is 7 kb in size. The information in the electronic format of the Sequence Listing is incorporated herein by reference in their entirety.

FIELD OF THE INVENTION

The present invention relates to methods for preventing and treating a proliferative disease, such as cancer, by modulating the arginine methyltransferase enzyme PRMT5 or by providing a E2F-1 protein which is arginine-methylation defective. The invention also relates to a method for identifying a proliferative disease which may be susceptible to this method of treatment and a screening method for identifying substances useful for the treatment of a proliferative disease.

BACKGROUND OF THE INVENTION

E2F is a family of transcription factors implicated in a variety of cell fates including proliferation, apoptosis and differentiation (Stevens and La Thangue; 2003; Frolov and Dyson 2004, Polager and Ginsberg 2008; van den Heuvel and Dyson 2008). E2F proteins share the capacity to regulate a diverse group of target genes (Frolov and Dyson 2004; van den Heuvel and Dyson 2008). The first family member identified, E2F-1, physically interacts with the retinoblastoma tumour suppressor protein pRb, which negatively regulates E2F-1 activity (Bandara and La Thangue 1991; Zamanian and La Thangue 1992; Weinberg 1995; Stevens and La Thangue 2003). Whilst it is established that E2F-1 can promote proliferation, it has also become clear that E2F-1 can prompt apoptosis (van den Heuvel and Dyson 2008, Polager and Ginsberg 2008). In Rb−/− mice, the enhanced levels of apoptosis in certain tissues reflect deregulated E2F-1 activity (Tsai et el 1998; Iaquinta and Lees 2007). Further, E2F-1−/− mice suffer from an increased incidence of tumours (Field et al 1996), suggesting that E2F-1 adopts a tumour suppressor role in some tissues, perhaps reflecting its ability to induce apoptosis. However, the mechanisms that influence the diverse cellular outcomes that have been ascribed to E2F-1 activity, particularly its apoptotic activity and the cell context dependency of these events, remain elusive. It is an object of the invention to identify such mechanisms. Not only is E2F-1 regulated during cell cycle progression (Stevens and La Thangue, 2003, van den Heuvel and Dyson 2008), but also under conditions of DNA damage (Pediconi et al 2003; Stevens et at 2003; Stevens and La Thangue 2003). In DNA damaged cells, E2F-1 is induced in a fashion that follows similar kinetics to p53 (Pediconi et al 2003; Stevens and La Thangue 2003), which co-incides with activation of a diverse collection of E2F target genes (Ren et al 2002). DNA damage activates a signal transduction pathway involving protein phosphokinases, such as ATM/ATR and Chk1/Chk2, which in turn phosphorylate effector proteins that mediate the outcome of the DNA damage response (Jackson and Bartek, 2009). Both families of DNA damage responsive kinases phosphorylate E2F-1, which contributes to the regulation of E2F-1 in DNA damaged cells (Stevens et al 2003; Stevens and La Thangue 2003). Moreover, E2F-1 prompts apoptosis under DNA damage conditions and, in tumour cells which harbour compromised p53 activity, might provide an important pathway that enables apoptosis to be activated (Stevens and La Thangue 2003).

Arginine methylation is established as an important type of modification in protein control (Bedford and Richard 2005). A variety of processes are influenced by arginine methylation, including RNA splicing, chromatin and transcription control (Meister et al 2001; Pal et al 2004; Bedford and Richard 2005). It has been established that the p53 tumour suppressor protein is regulated by arginine methylation, and defined a role for the protein arginine N-methyltransferase 5 (PRMT5) (Janson et al 2008). Significantly, arginine methylation occurred in DNA damaged cells, and influenced the outcome of the p53 response (Janson et al 2008).

Cancer (and other hyperproliferative disease) is characterised by uncontrolled cellular proliferation. It is an object of the present invention to provide an alternative strategy for treating cancer and other proliferative diseases. Specifically it is an object of the invention to identify mechanisms that may be manipulated to lead to the death of tumour cells and other cells that proliferate abnormally. It is a further object of the invention to provide screening methods for identifying compounds that may be useful in the treatment of these conditions. It is a further object of the invention to identify a biomarker to identify responsive tumours.

SUMMARY OF THE INVENTION

According to a first aspect the invention provides a method for the treatment of a proliferative disease comprising administering a substance which reduces the expression and/or activity of the enzyme PRMT5. Preferably the substance reduces the catalytic activity of PRMT5. In particular the substance preferably reduces or abolishes the ability of PRMT5 to methylate E2F1 protein. Advantageously, this method provides a new therapeutic strategy which is not currently exploited by any available therapeutic agent. This will also allow combination therapies with existing drugs which have very different mechanisms of action.

In one embodiment, the method comprises antisense or RNA interference (RNAi). Preferably, the method comprises administering an antisense molecule, an shRNA or an siRNA, for example an oligonucleotide comprising the sequence: 5' CCGCUAUUGCACCUUGGAA (SEQ ID NO:1), or a sequence with at least 90% identity thereto, or 5 ' CAACA-GAGAUCCUAUGAUU (SEQ ID NO:2), or a sequence with at least 90% identity thereto. Such oligonucleotides may be modified to improve their stability and/or potency and/or may be modified to enable systemic delivery.

In another embodiment the method comprises administering a small molecule inhibitor of PRMT5.

According to another aspect the invention provides a method for the treatment of a proliferative disease comprising providing an E2F-1 protein which is arginine-methylation defective. This approach relates directly to the E2F-1 protein whereas the PRMT5 approach has an indirect effect on the E2F-1 protein with equivalent end results.

According to another aspect the invention provides a substance which reduces the expression or activity of the enzyme PRMT5 for the treatment of a proliferative disease and the use of a substance which reduces the expression or activity of the enzyme PRMT5 for the manufacture of a medicament for the treatment of a proliferative disease.

According to a further aspect the invention provides an antibody which specifically binds to arginine-methylated E2F-1 protein, for example an antibody which specifically binds to a peptide comprising a sequence according to SEQ ID NO:5 or SEQ ID NO:6. Such an antibody may be used to detect E2F-1 methylation and in a method of identifying a proliferative disease which may be susceptible to treatment by the inhibition of PRMT5.

According to yet another aspect the invention provides a method of determining if a subject will benefit from treatment with a PRMT5 inhibitor comprising evaluating a biological sample from said subject for the presence and/or concentration of methylated E2F-1 protein, wherein the presence of methylated E2F-1 protein indicates that the subject will benefit from treatment with a PRMT5 inhibitor, or wherein an elevated concentration of methylated E2F-1 protein in the biological sample indicates that the subject will benefit from treatment with a PRMT5 inhibitor. Alternatively the presence and/or concentration of PRMT5 protein may be used as a biomarker for identifying responsive tumours in such a method.

According to another aspect, the invention provides a method of determining the prognosis of a subject comprising evaluating a biological sample from said subject for the presence and/or concentration of methylated E2F-1 protein and/or PRMT5 protein.

Further, the invention provides a kit for use in identifying a proliferative disease which may be susceptible to treatment by the inhibition of PRMT5, or for determining if a subject will benefit from treatment with a PRMT5 inhibitor, or for determining the prognosis of a subject, comprising an antibody as defined herein, or epitope-binding fragment thereof.

Further, the invention provides a method for screening for a substance, or a salt or a solvate thereof, to be used in the prevention or treatment of a proliferative disease, which comprises the following steps:
(i) incubating PRMT5 and E2F-1 with and without a substance of interest, and
(ii) measuring the amount of arginine methylation of E2 F-1,
(iii) comparing the amount of arginine methylation of E2F-1 without incubation of the test substance with the amount of arginine methylation of E2F-1 with incubation of the test substance, wherein a decrease in the amount of arginine methylation of E2F-1 indicates that the substance may be useful in the prevention or treatment of cancer.

DETAILED DESCRIPTION OF THE INVENTION

Figure 1:
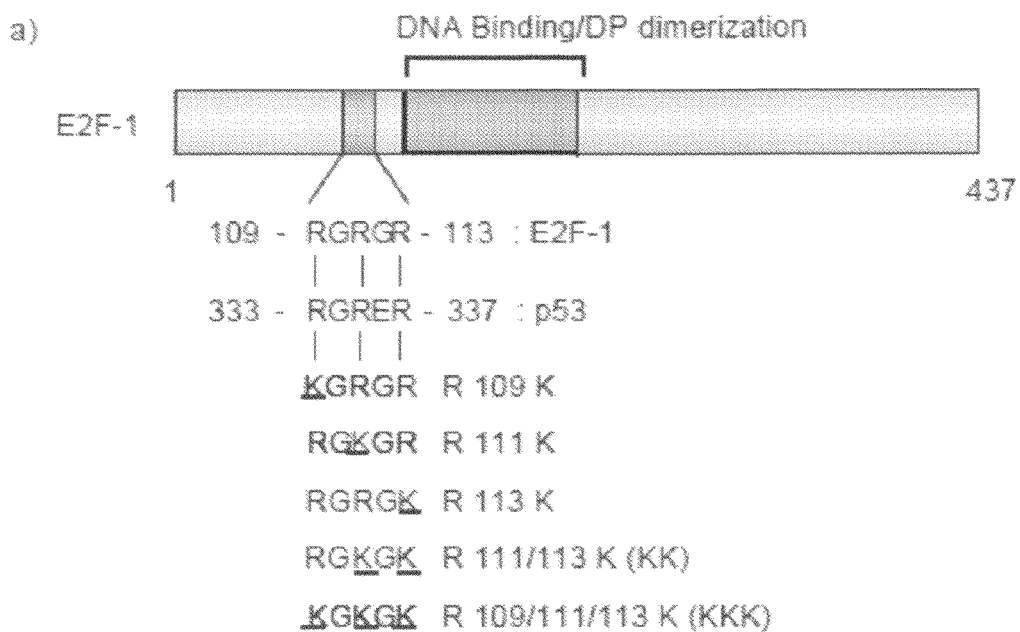
FIGS. 1a-1e show that E2F-1 undergoes arginine methylation by PRMT5. The sequences in FIG. 1a from top to bottom are SEQ ID NO:4, SEQ ID NO:14, SEQ ID NO:15, SEQ ID NO:16, SEQ ID NO:17, SEQ ID NO:18 and SEQ ID NO:19.
Figure 1:
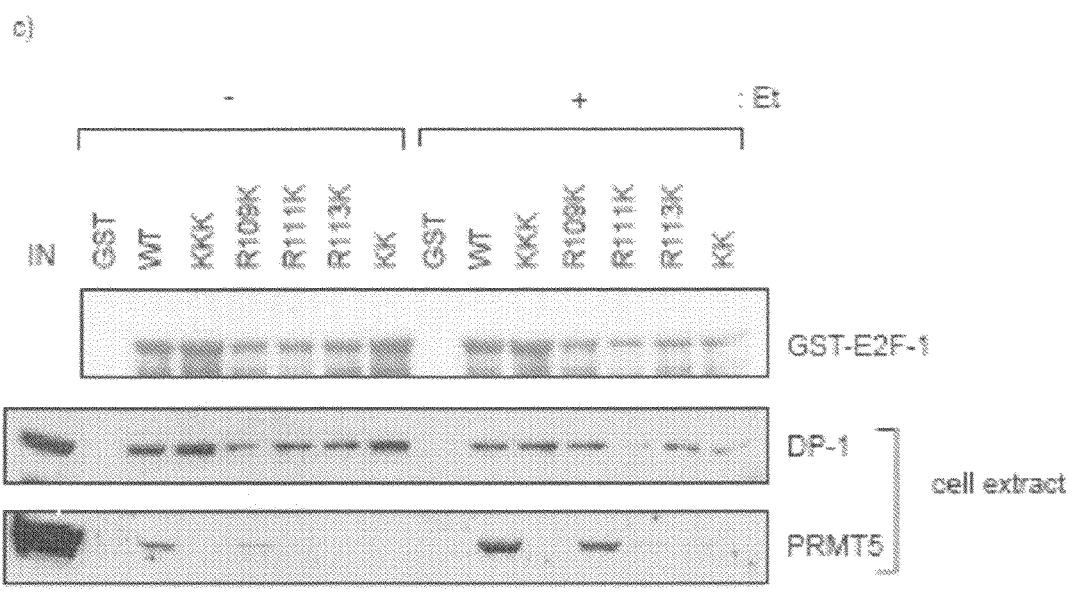
Figure 1:
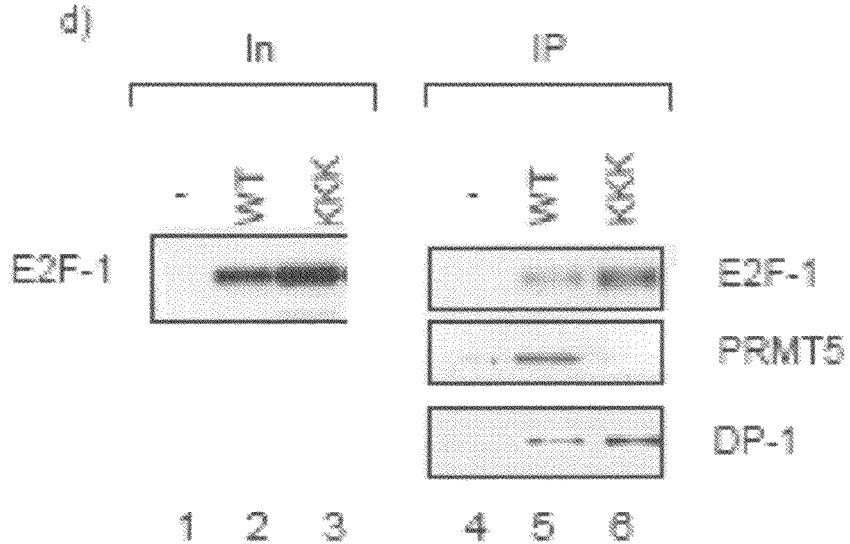
Figure 1:
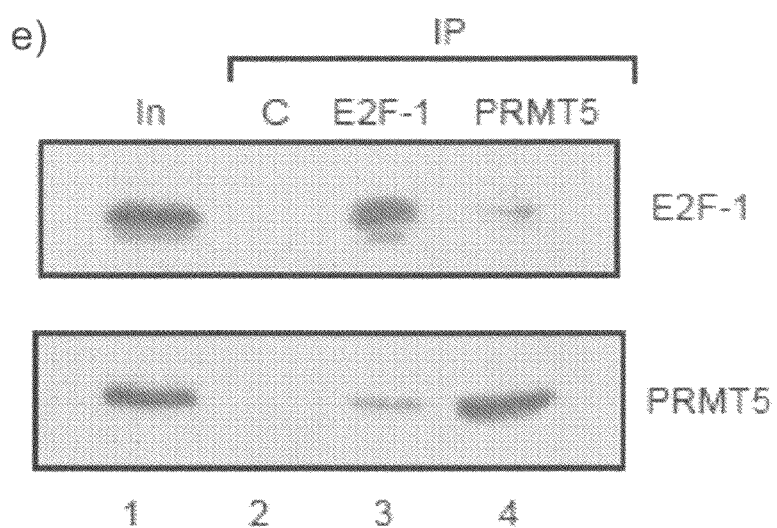

The invention is based on a novel mechanism for targeting and controlling the E2F pathway, by arginine methylation. It is shown herein that PRMT5 methylates E2F-1 and that arginine methylation is a key regulator of E2F-1 activity. Specifically, an arginine methylation defective E2F-1 protein exhibits increased protein stability, and activates transcription and induces apoptosis more effectively than wild-type E2F-1 . Moreover, PRMT5 methylation down-regulates E2F-1 levels, which in turn enables PRMT5 to suppress E2F-1 -dependent apoptosis. These results establish a new mechanism that controls the apoptotic properties of E2F-1 , and more generally suggest that arginine methylation contributes to the context dependency and cellular consequence of E2F-1 activation.

Accordingly, methods are described herein in which the expression and/or activity of the PRMT5 enzyme is reduced, thereby promoting E2F-1 -dependent apoptosis. Advantageously, this method may be useful in killing tumour cells, and other cells which proliferative abnormally, or hyperproliferate, which contain methylated E2 F-1.

According to a first aspect the present invention provides a method for the treatment of a proliferative disease comprising administering a substance which reduces the expression and/or activity of the enzyme PRMT5. Such a substance may be referred to herein as a 'PRMT5 inhibitor'.

The sequence information for PRMT5 may be found at the National Center for Biotechnology Information (http colon// www dot ncbi dot nlm dot nih dog gov / pubmed;) under accession numbers NM_006109 (nucleotide) and NP_006100 (protein).

By 'reduces the expression and/or activity of the enzyme' it is meant that expression of the enzyme is reduced or inhibited and/or that the activity of the enzyme is reduced partially or completely. Expression of the enzyme may be altered by gene therapy or by disrupting transcription of the gene encoding the enzyme or by destruction of the gene transcript or by disrupting translation or by degradation of the enzyme. The activity of the enzyme may be altered by a competitive or non-competitive inhibitor, or by genetic modification. Preferably the substance reduces the catalytic activity of PRMT5. In particular the substance preferably reduces or abolishes the ability of PRMT5 to methylate E2F1 protein.

Preferably the method provides a reduction in the amount of active enzyme of from 10% to 100% based on the amount of active enzyme in the cell prior to treatment. Most preferably the method provides a reduction in the amount of active enzyme of at least 20%, at least 30%, at least 40%, at least 50%, at least 60%, at least 70%, at least 80%, at least 90%, at least 95%, or at least 99%, based on the amount of active enzyme in the cell prior to treatment. The amount of active enzyme may be quantitated by measuring the enzyme activity in the cell or in an in vitro assay. For example, a recombinant PRMT5 enzyme may be expressed and the activity of methyltransferases measured in vitro, as described, for example, in Example 1, FIG. 1b and the Materials and Methods.

In accordance with the invention, the substance to be administered may comprise a small molecule drug or a peptide which may be designed to inhibit the activity of PRMT5 or to block the methylation of E2F-1 at one or more of the arginine residues at positions 109, 111 or 113 of the protein. Methylated E2F-1 refers to an E2F-1 protein which is methylated on 1 or more of residues R109, R111 and 8113. Preferably, methylated E2F-1 is di-methylated on two residues of E2F-1 selected from residues R109, R111 and R113. Most preferably methylated E2F-1 is di-methylated on residues R111 and R113. Preferably the methylation is symmetric.

Alternatively the method may comprise the use of antisense or RNA interference (RNAi) technology to reduce expression of the PRMT5 protein. For example, an antisense molecule, a short hairpin RNA (shRNA) or a small interfering RNA (siRNA) may be administered in accordance with the method of the invention, in order to downregulate expression of PRMT5. Antisense, shRNA and siRNA technologies are known to the skilled person and are described in Goyal 2009, Hajeri 2009, Oh 2009, Singh 2009, Rao 2009, Tilesi 2009, Singer 2008 and Bernards 2006, all of which are incorporated herein by reference.

An antisense molecule preferably comprises a single-stranded oligonucleotide of approximately 12 to 20 nucleotides in length, most preferably about 16 nucleotides. A small interfering RNA (siRNA) preferably comprises a double stranded oligonucleotide of approximately 14 to 22 base pairs in length, most preferably 16 to 20 base pairs in length. For example the siRNA may comprise a double stranded olionucleotide of 16, 17, 18, 19 or 20 base pairs in length. The siRNA may have a single or double overhang at one or both ends, i.e. a 3' or 5' overhang consisting of one or two bases.

An antisense or siRNA molecule may be designed based on the mRNA sequence that encodes the target protein, namely the PRMT5 enzyme. Preferably the antisense or siRNA molecule is complementary to a section of the mRNA sequence that encodes the target protein. The design of siRNA molecules is known in the art (e.g. Tilesi 2009) and there are websites which may be used for designing siRNA, for example: http colon // www dot dharmacon dot com / DesignCenter / DesignCenterPage dot aspx.

A series of oligonucleotides may be designed and tested against the target mRNA (i.e. PRMT5 mRNA) and a reduction in the amount of target mRNA looked for. The levels of mRNA can be measured directly or indirectly by monitoring PRMT5 protein levels, by known techniques.

A preferred siRNA for use in accordance with the invention comprises the sequence 5' CCGCUAUUGCACCUUGGAA (SEQ ID NO:1) or a sequence with at least 60%, at least 70%, at least 80%, at least 90%, at least 95% or at least 99% identity thereto. Another preferred siRNA for use in accordance with the invention comprises the sequence 5' CAACAGAGAUCCUAUGAUU (SEQ ID NO:2) or a sequence with at least 60%, at least 70%, at least 80%, at least 90%, at least 95% or at least 99% identity thereto.

An 'oligonucleotide' or 'oligo' shall mean multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). The term 'oligonucleotide' as used herein refers to both oligoribonucleotides and oligodeoxyribonucleotides. The term 'oligonucleotide' shall also include oligonucleosides (i.e. an oligonucleotide minus the phosphate) and any other organic base containing polymer. Oligonucleotides can be obtained from existing nucleic acid sources (e.g. genomic or cDNA), but are preferably synthetic (e.g. produced by oligonucleotide synthesis).

In preferred embodiments the oligonucleotide may be modified to improve its stability and/or potency. A 'stabilized oligonucleotide' shall mean an oligonucleotide that is more resistant to in vivo degradation (e.g. via an exo- or endonuclease) than the same oligonucleotide which is not stabilized, for example it may be degraded at least 2, 3, 4 or 5 times more slowly than the non-stabilized oligonucleotide. Preferred stabilized oligonucleotides of the invention have a modified phosphate backbone. Especially preferred oligonucleotides have a phosphorothioate modified phosphate backbone (i.e. at least one of the phosphate oxygens is replaced by sulfur). Other stabilized oligonucleotides include: nonionic DNA analogs, such as alkyl- and arylphosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

Other ways to increase the stability and/or potency of the oligonucleotide include 2'—O modifications and/or LNA modifications.

In other preferred embodiments the oligonucleotide may be modified to promote local, topical or systemic delivery. For example, it may be conjugated to an aptamer, formulated in a lipid nanoparticle such as a liposome, polyconjugated, conjugated to a lipophilic molecule such as cholesterol, contained in a cyclodextrin nanoparticle or complexed with an antibody. To promote systemic delivery the oligonucleotide is preferably modified in one of these ways. These and other suitable modifications are described by Toudjarska and de Fougerolles 2009.

In an alternative embodiment of the invention, a gene therapy approach may be taken, in which an E2F-1 protein which is arginine-methylation defective is provided. The sequence information for E2F-1 may be found at the National Center for Biotechnology Information (http colon // www dot ncbi dot nlm dot nih dot gov / pubmed) under accession numbers NM_005225 (nucleotide) and NP_005216 (protein). The protein sequence is reproduced here as SEQ ID NO:3:

```
  1  MALAGAPAGG  PCAPALEALL  GAGALRLLDS  SQIVIISAAQ
     DASAPPAPTG  PAAPAAGPCD

61  PDLLLFATPQ  APRPTPSAPR  PALGRPPVKR  RLDLETDHQY
     LAESSGPARG  RGRHPGKGVK

121  SPGEKSRYET  SLNLTTKRFL  ELLSHSADGV  VDLNWAAEVL
     KVQKRRIYDI  TNVLEGIQLI

181  AKKSKNHIQW  LGSHTTVGVG  GRLEGLTQDL  RQLQESEQQL
     DHLMNICTTQ  LRLLSEDTDS

241  QRLAYVTCQD  LRSIADPAEQ  MVMVIKAPPE  TQLQAVDSSE
     NFQISLKSKQ  GPIDVFLCPE

301  ETVGGISPGK  TPSQEVTSEE  ENRATDSATI  VSPPPSSPPS
     SLTTDPSQSL  LSLEQEPLLS

361  RMGSLRAPVD  EDRLSPLVAA  DSLLEHVRED  FSGLLPEEFI
     SLSPPHEALD  YHFGLEEGEG

421  IRDLFDCDFG  DLTPLDF
```

An E2F-1 protein which is arginine-methylation defective is mutated so that one or more of residues 8109, R111 and R113 are substituted with residues that are resistant to methylation. Preferably the arginine (R) residue(s) are substituted with lysine (K) residue(s). Preferably the methylation-defective E2F-1 protein contains the mutations R111K and R113K (the 'KK mutant') or R109K, R111K and R113K (the 'KKK mutant'). Accordingly the invention also provides a methylation-defective E2F-1 protein for the treatment of a proliferative disease and the use of a methylation-defective E2F-1 protein for the manufacture of a medicament for the treatment of a proliferative disease. Further the invention provides an oligonucleotide which encodes a methylation-defective E2F-1 protein for the treatment of a proliferative disease and the use of an oligonucleotide which encodes a methylation-defective E2F-1 protein for the manufacture of a medicament for the treatment of a proliferative disease.

The methods of the invention may be used in the treatment of a proliferative disease. As such, the methods may result in the killing of cells which proliferate abnormally, such as cancerous cells, including tumour cells, and other (non-malignant) tumour cells. The methods are particularly effective in killing cells which contain high levels of E2F-1 methylation. Thus, the invention provides methods for reducing E2F-1-mediated cell proliferation (e.g. tumour growth) in a patient.

High E2F-1 methylation may be defined by pathologists upon examining a biological sample (e.g. a tumour biopsy) from a patient. For example, a biological sample may be examined and given a total staining score (TSS). Total staining score is a parameter which is well-known to the skilled person. It is based upon the number of cells stained by an antibody specific for the antigen (in this case, methylated E2F-1 protein), the intensity of the staining in the cells and the overall pathology of the tumour (e.g. for bowel cancer the overall pathology may be defined as Dukes' stage A, B, C or D). A high level of E2F-1 methylation may then be defined as a TSS of at least 50%, preferably at least 60% or at least 70% or at least 80%.

The term 'proliferative disease' as used herein refers to both cancer and non-cancer disease. Preferably the proliferative disease is one characterized by increased methylation of the E2F-1 gene product in afflicted patients. Illustrative non-cancer diseases include inflammatory and/or immunoproliferative disorders such as arthritis, fibrosis, asthma and allergies. The invention can be used to screen for risk of and/or treat a variety of different types of cancer, particularly malignant (and preferably solid) tumours of epithelial or mesenchymal cells, e.g. an advanced solid tumour as disclosed in WO 02/66019. Examples of cancers that can be screened for risk of and/or treated by the present invention include brain and other central nervous system tumours (e.g. tumours of the meninges, brain, spinal cord, cranial nerves and other parts of central nervous system, e.g. glioblastomas or medulla blastomas); head and/or neck cancer; breast tumours; circulatory system tumours (e.g. heart, mediastinum and pleura, and other inbrathoracic organs, vascular tumours and tumour-associated vascular tissue); excretory system tumours (e.g. kidney, renal pelvis, ureter, bladder, other and unspecified urinary organs); gastrointestinal tract tumours (e.g. oesophagus, stomach, small intestine, colon, colorectal, rectosigmoid junction, rectum, anus and anal canal), tumours involving the liver and intrahepatic bile ducts, gall bladder, other and unspecified parts of biliary tract, pancreas, other and digestive organs); head and neck; oral cavity (lip, tongue, gum, floor of mouth, palate, and other parts of mouth, paroud gland, and other parts of the salivary glands, tonsil, oropharynx, nasopharynx, pyriform sinus, hypopharynx, and other sites in the lip, oral cavity and pharynx); reproductive system tumours (e.g. vulva, vagina, Cervix uteri, Corpus uteri, uterus, ovary, and other sites associated with female genital organs, placenta, penis, prostate, tests, and other sites associated with male genital organs); respiratory tract tumours (e.g. nasal cavity and middle ear, accessory sinuses, larynx, trachea, bronchus and lung, e.g. small cell lung cancer or non-small cell lung cancer); skeletal system tumours (e.g. bone and articular cartilage of limbs, bone articular cartilage and other sites); skin tumours (e.g. malignant melanoma of the skin, non-melanoma skin cancer, basal cell carcinoma of skin, squamous cell carcinoma of skin, mesothelioma, Kaposi's sarcoma); and tumours involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites, leukemias, including hairy cell leukemia, multiple myeloma, chronic lymphocytic leukemia, chronic myeloid leukemia, acute myeloid leukemia and acute lymphocytic leukemia, lymphomas, including non-Hodgkin's lymphoma and Hodgkin's lymphoma. Where hereinbefore and subsequently a tumour, a tumour disease, a carcinoma or a cancer is mentioned, also metastasis in the original organ or tissue and/or in any other location are implied alternatively or in addition, whatever the location of the tumour and/or metastasis is.

By 'treating a proliferative disease' it is intended to include the inhibition of the symptoms of a disease, namely, inhibition or retardation of the progression of the disease; and the alleviation of the symptoms of a disease, namely, regression of the disease or the symptoms, or inversion of the progression of the symptoms. It may also include the prevention of the development of a disease or a symptom from a patient who may have a predisposition of the disease or the symptom but has yet been diagnosed to have the disease or the symptom. By 'treating cancer' it is intended to include the inhibition of tumour growth, including the prevention of the growth of a tumour in a subject or a reduction in the growth of a pre-existing tumour in a subject. The inhibition can also be the inhibition of the metastasis of a tumour from one site to another. It is preferred to treat a tumour exhibiting high levels of PRMT5 protein and low levels of E2F-1 protein with a PRMT5 inhibitor in accordance with the invention, in order to inactivate PRMT5 and thereby activate E2F-1.

In other aspects the invention provides a substance which reduces the expression or activity of the enzyme PRMT5 for the treatment of a proliferative disease, for example cancer, and the use of a substance which reduces the expression or activity of the enzyme PRMT5 for the manufacture of a medicament for the treatment of a proliferative disease, for example cancer. Such substances are described above and may be formulated and administered as described herein.

Administration

In the treatment comprising the administration of a substance which reduces the expression and/or activity of the enzyme PRMT5, such substance may be mixed with a pharmaceutically acceptable carrier, so that it can be provided in the form of a pharmaceutical composition. Any ratio of active ingredient to carrier may be used and the ratio of an active ingredient to a carrier may preferably be between 1% and 90% by weight. In addition, the pharmaceutical composition of the present invention can be administered to humans or organisms other than humans [for example, non-human mammals (e.g. a bovine, a monkey, a chicken, a cat, a mouse, a rat, a hamster, a swine, a canine, etc.), birds, reptiles, amphibians, fish, insects, etc.] in various forms via either a topical, local or systemic administration route. For example, an oral administration route (including gavage, or admixture with food or drink) or a parenteral administration route (e.g. intravenous injection, intramuscular injection, subcutaneous administration, rectal administration, intraperitoneal, and dermal administration) may be used. Accordingly, as the pharmaceutical composition of the present invention, an active ingredient can be used singly. However, it is also possible to formulate such an active ingredient with a pharmaceutically acceptable carrier or diluent by a method commonly used depending on an administration route, so as to manufacture a formulation having a suitable dosage form. Any dosage form known to the skilled person may be used. Any appropriate carrier or diluent may be used, for example isotonic saline solution, buffers, etc. Such pharmaceutical carriers are well known in the art and the selection of a suitable carrier is deemed to be within the scope of those skilled in the art from the teachings contained herein.

The substance is administered in vivo in an amount effective to affect a decrease in the expression and/or activity of the enzyme PRMT5, as discussed above, and thereby induce apoptosis.

The term 'an effective amount' for purposes of this application shall mean that amount of substance capable of producing the desired effect. In this case, the desired effect may be the slowing of tumour growth, the death of tumour cells, reduction in the size of the tumour, regression of the condition, for example. The amount of substance which is given depends upon a variety of factors including the age, weight and condition of the patient, the administration route, the properties of the pharmaceutical composition, the condition of the patient, the judgment of a doctor, the condition and the extent of treatment or prevention desired. The substance may be administered to the individual as a short-term therapy or long-term therapy depending on the condition and the extent of treatment or prevention desired.

The substance which reduces the expression and/or activity of the enzyme PRMT5 may be employed alone or in combination with other techniques, drugs or compounds for preventing, controlling or treating the profilerative disease. For example, for the treatment of cancer the substance may be administered in combination (e.g. contemporaneously or sequentially) with chemotherapeutic agents, cytostatic agents, antiangiogenic agents, radiation or anti-neoplastic agents, such as doxorubicin, cisplatin, taxotere, 5-fluoruracil, methotrexat, gemzitabin and cyclophosphamide.

The oligonucleotides used in the methods of the invention may be formulated as a pharmaceutical composition as described above or may be administered using gene therapy. In the gene therapy of the present invention, it may be possible to select either an in vivo method of directly administering a recombinant vector encoding the oligonucleotide of interest to a patient, or an ex vivo method of collecting a target cell from a patient body, introducing the oligonucleotide of interest, or a recombinant vector encoding the oligonucleotide of interest, into the target cell outside of the body, and returning the target cell, into which the aforementioned oligonucleotide or vector has been introduced, to the patient body. In the case of the in vivo method, the recombinant vector encoding the oligonucleotide of interest is directly administered to a patient by using a gene transfer vector known in the present technical field, such as a retrovirus vector. As with the pharmaceutical composition of the present invention, such an oligonucleotide or gene transfer vector used in the gene therapy of the present invention can be mixed with a pharmaceutically acceptable carrier, so as to produce a formulation.

Such a formulation can be parenterally administered, for example. Fluctuation of a dosage level can be adjusted by standard empirical optimizing procedures, which are well understood in the present technical field. An alternative for in vivo administration is to use physical approaches, such as particle bombardment or jet injection, to directly deliver DNA encoding heavy and light chains of an engineered agonist antibody (Walther et al Mole Biotechnology 28:121-128, 2004; Yang et al PNAS 87:9568-72, 1990). In the case of the ex vivo method, such an oligonucleotide of interest can be introduced into a target cell according to a method known in the present technical field, such as the calcium phosphate method, the electroporation method, or the viral transduction method. Such a target cell can be collected from the affected region, e.g. tumour. In the case of selecting the ex vivo method an oligonucleotide of interest or a gene transfer vector to which the oligonucleotide of interest is operably linked is introduced into a cell, and the aforementioned oligonucleotide is then allowed to express in the cell. Thereafter, the cell is transplanted to a patient, so that the disease can be treated.

A gene transfer vector available for gene therapy is well known in the present technical field, and it can be selected, as appropriate, depending on a gene introduction method or a host. Examples of such a vector include an adenovirus vector and a retrovirus vector. When an oligonucleotide is ligated to a gene transfer vector, a control sequence such as a promoter or a terminator, a signal sequence, a polypeptide-stabilizing sequence, etc. may be appropriately ligated, such that the oligonucleotide can be expressed in a host. Selection or construction of such vectors is well known to the skilled person.

The administration and gene therapy techniques described above are also applicable for the gene therapy approach, in which an E2F-1 protein which is arginine-methylation defective is provided. In this case an E2F-1 gene encoding the arginine-methylation defective protein is inserted into a gene transfer vector and administered by any suitable method known to the skilled person. This approach may be employed alone or in combination with other techniques, drugs or compounds for preventing, controlling or treating the profilerative disease. For example, for the treatment of cancer the substance may be administered in combination (e.g. contemporaneously or sequentially) with chemotherapeutic agents, cytostatic agents, antiangiogenic agents, radiation or anti-neoplastic agents, such as doxorubicin, cisplatin, taxotere, 5-fluoruracil, methotrexat, gemzitabin and cyclophosphamide.

Biomarker

In a further apect, the invention provides an antibody which specifically binds to arginine-methylated E2F-1 protein. Preferably the antibody specifically binds to a methylated E2F-1 peptide comprising or consisting of the sequence RGRGR (SEQ ID NO:4) in which one or more of the arginine residues is methylated, for example the sequence RGR(Me)GR(Me) (SEQ ID NO:5). Most preferably the antibody specifically binds to a methylated E2F-1 peptide comprising or consisting of the sequence CESSGPARGR(Me)GR(Me)HPGKG (SEQ ID NO:6).

The term 'antibody' as used herein includes all forms of antibodies such as recombinant antibodies, humanized antibodies, chimeric antibodies, single chain antibodies, polyclonal antibodies, monoclonal antibodies etc. Preferably the antibody is a monoclonal antibody. The invention is also applicable to antibody fragments and derivatives that are capable of binding to the antigen.

The skilled person could make such antibodies by known methods. Various forms of antibodies can be made using standard recombinant DNA techniques (Winter and Milstein, Nature, 349, pp. 293-99 (1991)). For example, the production of rat proteolytic fragments of IgG antibodies is described by Rousseaux, J (Methods in Enzymology 1986; 121; 663). Antibodies: A Laboratory Manual (Ed Harlow, Edward Harlow, David Lane, CSHL Press, 1988) describes obtaining fragments of human antibodies. Gilliland et at (Tissue Antigens 1996; 47(1):1-20) describes a general method for isolating the variable regions of antibodies and the production of a chimeric antibody. The preparation of monoclonal antibodies is a well-known process (Kohler et al., Nature, 256:495 (1975)).

Chimeric and humanised, e.g. CDR-grafted, antibodies may be used in accordance with the present invention. These antibodies are less immunogenic than the corresponding rodent antibodies. Thus, the antibody may have CDRs which are of different origin to the variable framework region. Similarly, the antibody may have CDRs of different origin to the constant region.

Preferred antibodies according to the present invention are such that the affinity constant for the antigen is $10^5$ mole$^{-1}$ or more, for example up to $10^{12}$ mole$^{-1}$. Ligands of different affinities may be suitable for different uses so that, for example, an affinity of $10^6$, $10^7$, $10^8$, $10^9$, $10^{10}$ or $10^{11}$ mole$^{-1}$ or more may be appropriate in some cases. However antibodies with an affinity in the range of $10^6$ to $10^8$ mole$^{-1}$ will often be suitable. Conveniently the antibodies also do not exhibit any substantial binding affinity for other antigens, in particular antigens which are not methylated but which otherwise have the same sequence as the desired antigen. Specifically, the antibody preferably specifically binds to E2F-1 which is methylated on one or more arginine residues but does not bind to unmethylated E2F-1.

Binding affinities of the antibody and antibody specificity may be tested by assay procedures such as radio labelled or enzyme labelled binding assays and use of biacore with solid phase ligand. (Bindon, C. I. et al: 1988 Eur. J. Immunol. 18, 1507-1514; Dall'Acqua, W., et al. Biochemistry 35, 9667; Luo et al. J. Immunological Methods 275 (2203) 31-40; Murphy et al. Curr Protoc Protein Sci. 2006 September; Chapter 19: Unit 19.14).

The antibody may be used to measure E2F-1 methylation, which can be used as a biomarker. In particular, the antibody may be used in a method of identifying patients which may benefit from treatment by the method described above. Accordingly, the invention provides a method of identifying a proliferative disease (for example a tumour) which may be susceptible to treatment by the inhibition of PRMT5 which comprises the use of an antibody which specifically binds to arginine-methylated E2F-1 protein.

The invention also provides a method of determining if a subject will benefit from treatment with a PRMT5 inhibitor comprising the steps of evaluating a biological sample from said subject for the presence and/or concentration of methylated E2F-1 protein, wherein the presence of methylated E2F-1 protein indicates that the subject will benefit from treatment with a PRMT5 inhibitor, or wherein an elevated concentration of methylated E2F-1 protein in the biological sample indicates that the subject will benefit from treatment with a PRMT5 inhibitor.

The invention further provides a method of determining if a subject will benefit from treatment with a PRMT5 inhibitor comprising evaluating a biological sample from said subject for the presence and/or concentration of PRMT5 protein, wherein the presence of PRMT5 protein indicates that the subject will benefit from treatment with a PRMT5 inhibitor, or wherein an elevated concentration of PRMT5 protein in the biological sample indicates that the subject will benefit from treatment with a PRMT5 inhibitor.

The biological sample may be a solid or body fluid sample. The biological sample may include cells, blood, plasma or serum. Preferably the biological sample is a tissue biopsy or serum or circulating tumour cells. Examples of solid biological samples include samples taken from faeces, the rectum, central nervous system, bone, breast tissue, renal tissue, the uterine cervix, the endometrium, the head/neck, the gallbladder, parotid tissue, the prostate, the brain, the pituitary gland, kidney tissue, muscle, the esophagus, the stomach, the small intestine.

The method of the invention can be used to detect methylated E2F-1 protein and/or PRMT5 protein in a biological sample in vitro or in vivo. The presence and/or concentration of methylated E2F-1 protein and/or PRMT5 protein may be determined by standard immunochemical techniques which are well known to the skilled person (for example immunohistochemistry, radioimmunoassay, ELISA, Western blot, fluorescence assay, etc).

In one embodiment, the method of the invention is used to determine the level of methylated E2F-1 protein and/or PRMT5 protein in a tissue or in cells derived from the tissue. In a preferred embodiment, the tissue is a diseased tissue. In a preferred embodiment of the method, the tissue is a tumour or a biopsy thereof. In a preferred embodiment of the method, a tissue or a biopsy thereof is first excised from a patient, and the levels of methylated E2F-1 protein and/or PRMT5 protein in the tissue or biopsy can then be determined in an immunoassay with the antibodies or antibody fragments of the invention. The tissue or biopsy thereof can be frozen or fixed. The same method can be used to determine other properties of the methylated E2F-1 protein and/or PRMT5 protein, such as its cell surface levels, or its cellular localization.

This method requires assessing the presence and/or concentration of methylated E2F-1 and/or PRMT5 in order to determine whether the subject will benefit from treatment with a PRMT5 inhibitor. The skilled person willl understand that clinical material may be examined to understand how levels of methylated E2F-1 protein and/or PRMT5 protein relate to cancer. In some cases, the presence of methylated E2F-1 protein and/or PRMT5 protein will be indicative that the subject will benefit from treatment with a PRMT5 inhibitor. In other cases, an elevated concentration of methylated E2F-1 protein and/or PRMT5 protein will be indicative that the subject will benefit from treatment with a PRMT5 inhibitor. An elevated concentration is intended to be relative to a predetermined base level, which may be the level of methylated E2F-1 protein and/or PRMT5 protein in normal (i.e. noncancerous) biological samples from the subject or may be the level of methylated E2F-1 protein and/or PRMT5 protein in a sample or samples obtained from non-cancer-afflicted individuals. Preferably, a total staining score (TSS) of at least 50%, preferably at least 60% or at least 70% or at least 80%, as discussed above, may be indicative of the presence of E2F-1 methylation.

Preferably, a total staining score (TSS) of at least 50%, preferably at least 60% or at least 70% or at least 80%, as discussed above, may be indicative of an elevated concentration as compared to the predetermined base level, which may have a TSS of less than 50%, preferably less than 25%, preferably less than 10%, preferably close or equal to zero.

For example, the method may comprise the steps of:
(i) contacting a biological sample of said patient with an antibody as described herein, or epitope-binding fragment thereof, (ii) measuring the binding of said antibody or epitope-binding fragment thereof to said cells, and (iii) comparing the binding in part (ii) with that of a normal reference subject or standard.

The antibodies or antibody fragments of the invention can be used to detect methylated E2F-1 protein in a biological sample in vitro or in vivo as described above.

The above-described method can be used to diagnose a proliferative disease, for example cancer, in a subject known to or suspected to have a such a disease, wherein the level of methylated E2F-1 protein and/or PRMT5 protein measured in said patient is compared with that of a normal reference subject or standard. Said method can then be used to determine whether a tumour contains cells in which the E2F-1 protein is methylated, or which contains increased levels of PRMT5 protein, both of which may suggest that the tumour will respond well to treatment with the substances of the present invention.

Methylated E2F-1 protein and/or PRMT5 protein may also be used as a prognostic indicator. In this embodiment the levels of methylated E2F-1 protein and/or PRMT5 protein may be measured prior to treatment to predict the severity and progression of the disease. Optionally, the levels of methylated E2F-1 protein and/or PRMT5 protein may also be measured over a time course during and after treatment to monitor the progress of the disease and the success of any treatment. For example, high levels of methylated E2F-1 protein and/or PRMT5 protein may be indicative of a severe condition. For example, reduced levels of methylated E2F-1 protein and/or PRMT5 protein over a time period may be indicative of regression of the disease. For example, the longer the time it takes for the levels of methylated E2F-1 protein and/or PRMT5 protein to double (the doubling time), the better the prognosis for the patient. The levels of methylated E2F-1 protein and/or PRMT5 protein may be measured using the antibodies or antibody fragments. For example, the levels of methylated E2F-1 protein may be measured using the antibodies or antibody fragments of the invention or using any methods known to the skilled person. Accordingly, the invention further provides a method of determining the prognosis of a subject comprising evaluating a biological sample from said subject for the presence and/or concentration of methylated E2F-1 protein and/or PRMT5 protein.

Figure 7:
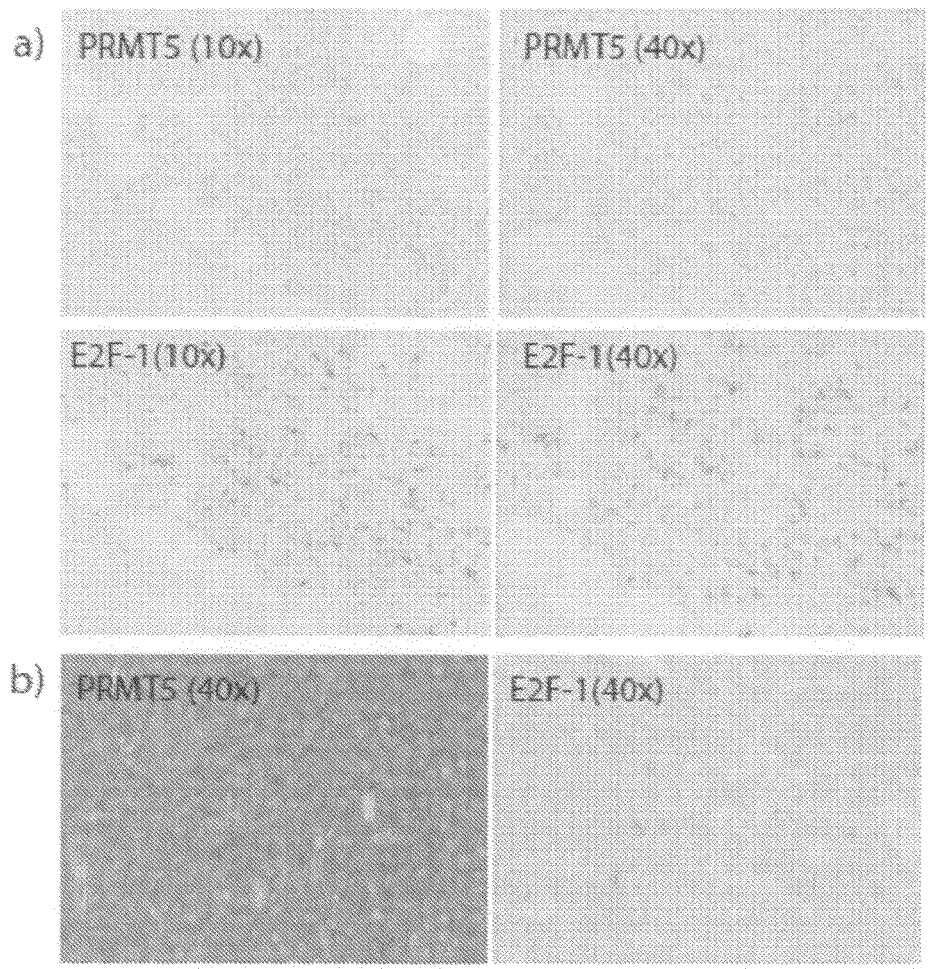
FIGS. 7a-7e show PRMT5 and E2F-1 expression in clinical tumour samples.
Figure 7:
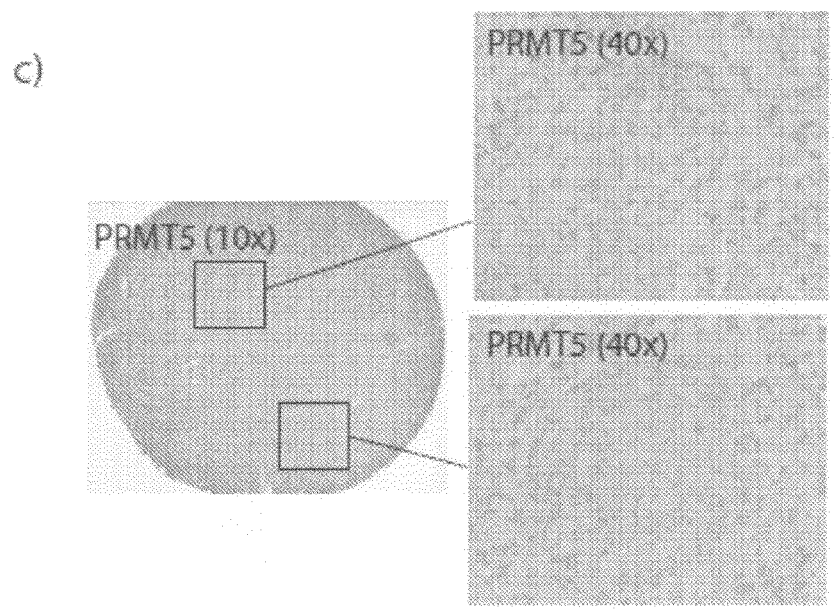
Figure 7:
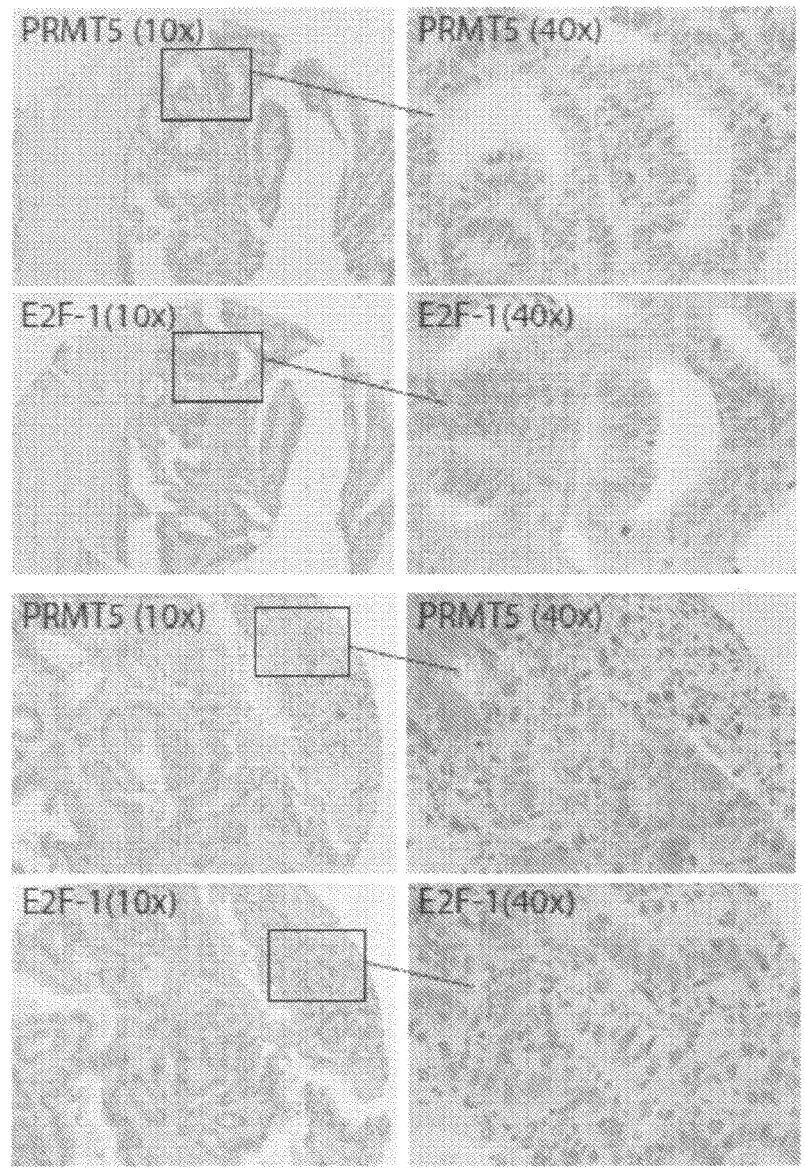
Figure 7:
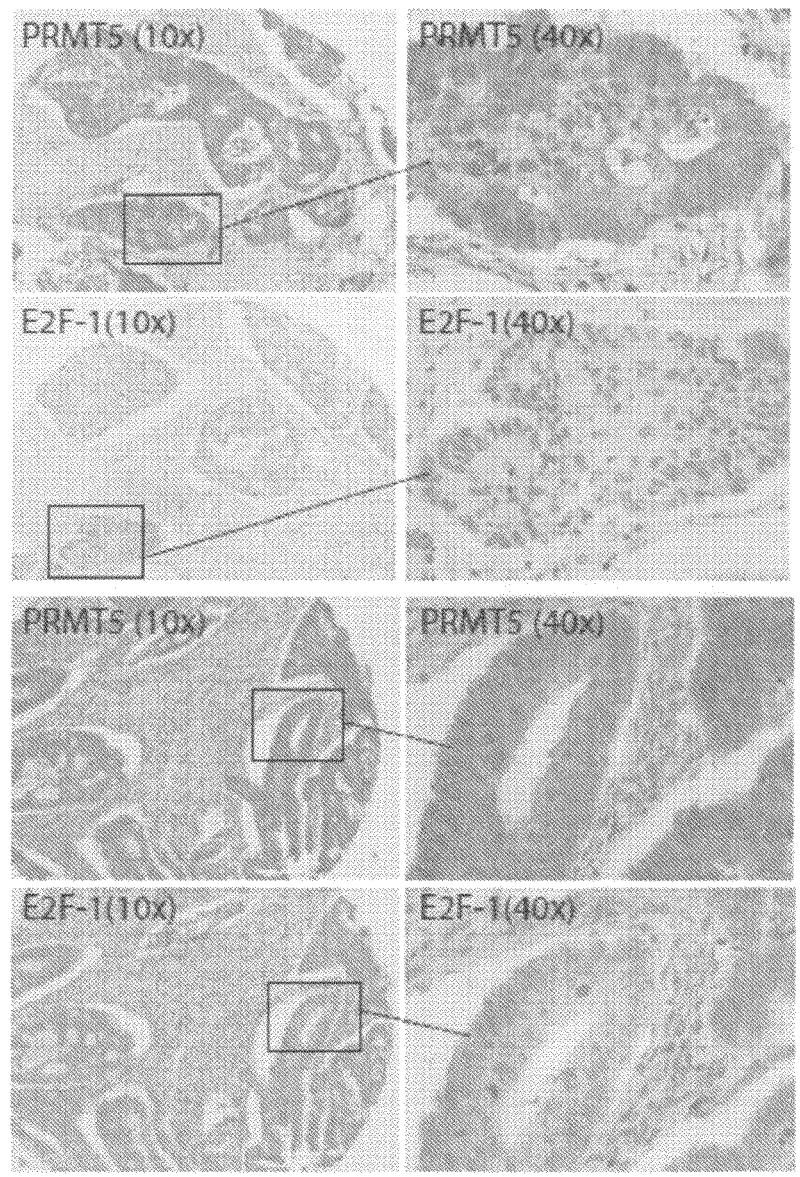

In accordance with the invention, it is preferred to treat a tumour which expresses high levels of PRMT5 and low levels of E2F-1. It is envisaged that in these tumours PRMT5 is suppressing E2F1 activity and thereby preventing apoptosis, and keeping cells in the proliferative mode. As such, the increase in E2F1 levels in a tumour may be used as a mechanistic endpoint biomarker for the effects of a PRMT5 inhibitor. The images in FIGS. 7d and 7e show that tumours exist with either high PRMT5/low E2F1 verses low PRMT5/high E2F1. It is preferred to treat the former with a PRMT5 inhibitor in accordance with the invention, in order to inactivate PRMT5 and thereby activate E2F1. Furthermore, a patient who has a tumour with high levels of PRMT5 and low levels of E2F-1 is likely to have an improved prognosis compared to a patient who has a tumour with low PRMT5/high E2F1.

The present invention further provides for monoclonal antibodies, humanized antibodies and epitope-binding fragments thereof that are further labelled for use in research, prognostic or diagnostic applications. In preferred embodiments, the label is a radiolabel, a fluorophore, a chromophore, an imaging agent or a metal ion. A method for diagnosis is also provided in which said labelled antibodies or epitope-binding fragments thereof are administered to a subject suspected of having a cancer, and the distribution of the label within the body of the subject is measured or monitored.

Kit

The present invention also includes kits, e.g., comprising a substance which reduces the expression and/or activity of the enzyme PRMT5 and instructions for the use of the substance for killing of particular cell types. The instructions may include directions for using the substance in vitro, in vivo or ex vivo.

Typically, the kit will contain a substance which reduces the expression and/or activity of the enzyme PRMT5 or a pharmaceutical composition comprising the substance. This may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the substance prior to administering to a patient, and tools that aid in administering the substance to a patient.

The present invention also includes a kit for use in identifying tumours which may be susceptible to treatment by the inhibition of PRMT5, or for determining if a subject will benefit from treatment with a PRMT5 inhibitor, or for determining the prognosis of a subject. The kit comprises an antibody as described here, or epitope-binding fragment thereof. The kit may also comprise means for obtaining a biological sample, such as a spatula or a dipstick or a container for accepting the sample. The kit may also comprise an assay for detecting the presence and/or concentration of methylated E2F-1 bound to the antibody. Preferably the assay comprises an immunoassay, such as an ELISA.

Screening Method

Accordingly, in another aspect the invention provides a screening method for identifying substances useful in the treatment of cancer. Specifically the invention provides a method for screening for a substance, or a salt or a solvate thereof, to be used in the prevention or treatment of cancer, which comprises the following steps:

(i) incubating PRMT5 and E2F-1 with and without a substance of interest, and (ii) measuring the amount of arginine methylation of E2F-1, (iii) comparing the amount of arginine methylation of E2F-1 without incubation of the test substance with the amount of arginine methylation of E2F-1 with incubation of the test substance, wherein a decrease in the amount of arginine methylation of E2F-1 indicates that the substance may be useful in the prevention or treatment of cancer. This method may be carried out in vitro.

The type of a substance screened by the screening method of the present invention is not particularly limited. Examples of such a substance include a therapeutic agent for treating cancer or a candidate compound therefor. A compound library is preferably used to provide for a high throughput screen. Preferably, substances may be selected as potential inhibitors by rational design based on the crystal structure of PRMT5. Molecules may be selected using a variety of computational approaches (for example substructure searching, similarity searching and shape-based screening).

The method may be carried out in cells or a cell-free system. Any cell type may be used in accordance with the invention, for example 3T3 cells, 293 cells, 721 cells, B16 cells, CHO cells, COS-7 cells, N1H-3T3 cells, and so on. Preferred are cancer cell lines, for example the human osteosarcoma cell line U2OS, the cervical cancer cell lines HeLa and C33A, the breast cancer cell lines MCF-7 and MDA-MB-438, the prostate cancer lines PC3 and LNCap, Saos-2 cells, and so on. Cells are plated and incubated to form monolayers in any manner known to the skilled person. For example $1\times10^5$ cells may be plated into 24-well plates and incubated for 18 hours to form monolayers.

PRMT5 and E2F-1 proteins may be obtained by expression in cells or by recombinant expression in vitro. For example, a plasmid containing the PRMT5 and/or E2F-1 genes may be transfected into cells. Subsequently, the cells may be lysed and the PRMT5 protein immunoprecipitated (e.g. with agarose beads) and eluted. The proteins may be expressed as fusions proteins, for example Flag-PRMT5.

The E2F-1 peptide and PRMT5 enzyme may then be mixed with other recombinant substrates (such as GST fusion proteins or histones) in a methylation reaction buffer and with a methyl group donor (such as $^3$H labeled SAM) and incubated. For example, the methylation reaction buffer may contain 50 mM Tris, 0.1 mM EDTA and 50 mM NaCl. The —CH$_3$ group donor may be $^3$H labeled SAM. The reactants may be mixed to a volume of 40 µl. The reactants may be incubated at 30° C. for 90 min.

The presence and/or concentration of methylated E2F-1 may be determined by standard immunochemical techniques which are well known to the skilled person (for example immunohistochemistry, radioimmunoassay, ELISA, Western blot, fluorescence assay, DELFIA®, LANCE, FRET, etc). The method may preferably be carried out as a high throughput screen. The amount of arginine methylation of E2F-1 without incubation of the test substance is compared with the amount of arginine methylation of E2F-1 with incubation of the test substance. A decrease in the amount of arginine methylation of E2F-1 indicates that the substance may be useful in the prevention or treatment of cancer.

EXAMPLES

The following examples are illustrative of the products and methods falling within the scope of the present invention. They are not to be considered in any way limitative of the invention.

Example 1

E2F-1 is Methylated by PRMT5

A comparison with p53 identified a sequence motif in E2F-1, RGRGR, with similarity to the known sites of arginine methylation in p53, namely RGRER. FIG. 1A shows the location of E2F-1 RGRGR sequence motif in E2F-1, highlighting the similarity with the region in p53 targeted by PRMT5 (Jansson et al 2008). It is consistent with this observation that wild-type E2F-1 could be methylated in vitro by the arginine methyltransferase PRMT5.

To assess whether the RGRGR motif was a direct target for PRMT5 methylation, a series of mutant derivatives of E2F-1 were made in which each arginine (R) residue was substituted with a lysine residue (K; FIG. 1a), and the ability of the mutant derivative to be methylated in vitro then assessed. FIG. 1b shows the in vitro methylation of E2F-1 and the various mutant derivitives. In FIG. 1b(i) each of the indicated proteins (about 1 µg) was used in the methylation reaction. In vitro methylated samples were analysed by SDS-PAGE as described below. E2F-1 is indicated. In FIG. 1b(ii) samples in FIG. 1b(i) were counted (3H cpm as indicated). Histones treated with PRMT5 served as the positive control. The data shown provide one example taken from two different experiments.

It can be seen from FIG. 1b that mutation of any of the three R residues resulted in reduced methylation, although R111K and R113K exhibited a greater level of reduction compared to R109K. The double R111/113K (KK) and triple R109/111/113K (KKK) mutants could not be methylated by PRMT5, suggesting that R111 and R113 are the predominant sites of methylation. Histones methylated with Set7 served as a positive control.

It was then assessed whether E2F-1 could interact with PRMT5 and thereafter the role of each R residue in mediating the interaction. In an in vitro binding assay where GST-E2F-1 was incubated with cell extracts, wild-type E2F-1 bound to PRMT5. FIG. 1c shows the binding of E2F-1 to PRMT5. The indicated GST proteins were incubated with U2OS cell lysate, and bound proteins immunoblotted using anti-GST (for input GST), DP-1 or PRMT5 antibodies. Binding to DP-1, the major heterodimeric partner for E2F-1 (Stevens and La Thangue 2003), served as a control since it bound equally to each of the E2F-1 proteins. The single R111K and R113K substitution mutants exhibited compromised PRMT5 binding compared to the interaction between wild-type and PRMT5, whereas R109K exhibited significant PRMT5 binding activity, although a modest reduction was apparent. Both the KK and KKK mutants were completely devoid of PRMT5 binding, which co-incided with their inability to undergo methylation in vitro.

To establish whether E2F-1 was able to bind to PRMT5 in cells, the interaction between ectopic wild-type E2F-1 or KKK with PRMT5 was studied. FIG. 1d shows that E2F-1 and PRMT5 do interact in cells. Either a wild-type E2F-1 expression vector or a KKK expression vector was transfected into U2OS cells, and HA11 antibody was used for immunoprecipitation (IP) followed by immunoblotting with HA11 (E2F-1), PRMT5 or DP-1 as indicated. The level of input (In) protein is indicated. As seen in FIG. 1d wild-type E2F-1 co-immunoprecipitated with PRMT5, which was not apparent with the KKK mutant. In contrast, binding to DP-1 was equivalent for both wild-type E2F-1 and KKK. These results indicate that E2F-1 and PRMT5 interact in cells. Further, the RGRGR motif is necessary for the interaction, which also encompasses the site of PRMT5 methylation.

Next E2F-1 was immunoprecipitated with either anti-E2F-1 or anti-PRMT5 from U2OS cells and subsequently immunoblotted with anti-PRMT5 or anti-E2F-1 as indicated in FIG. 1e. The input (In) and control (−) immunoprecipitations are indicated. The results show that the endogenous proteins interact.

Example 2

E2F-1 is Methylated in Cells

Figure 2:
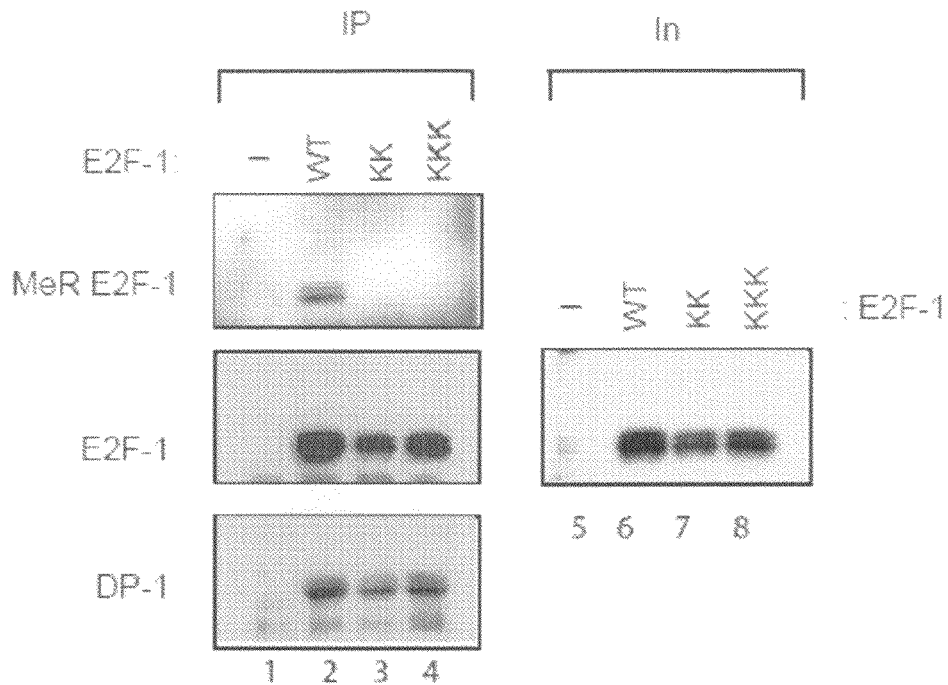
FIGS. 2a-2e show that E2F-1 is methylated on arginine residues under physiological conditions.
Figure 2:
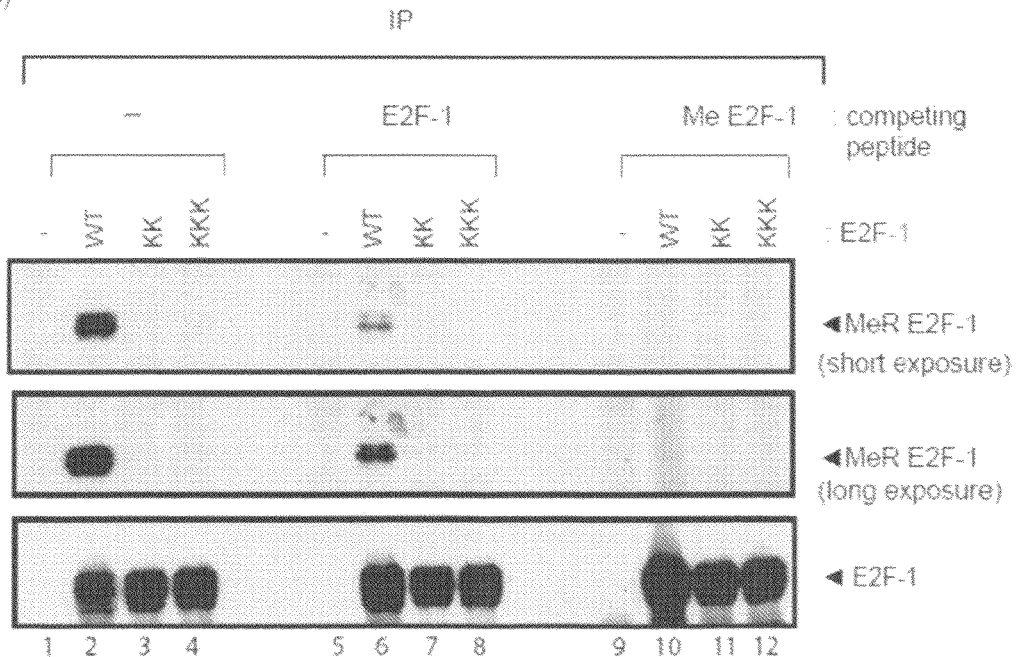
Figure 2:
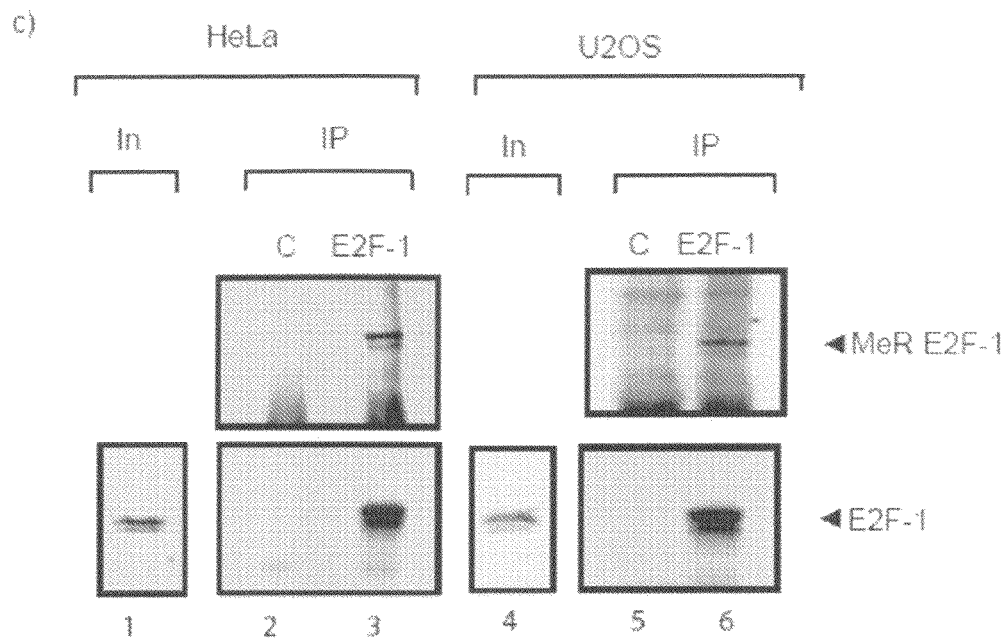
Figure 2:
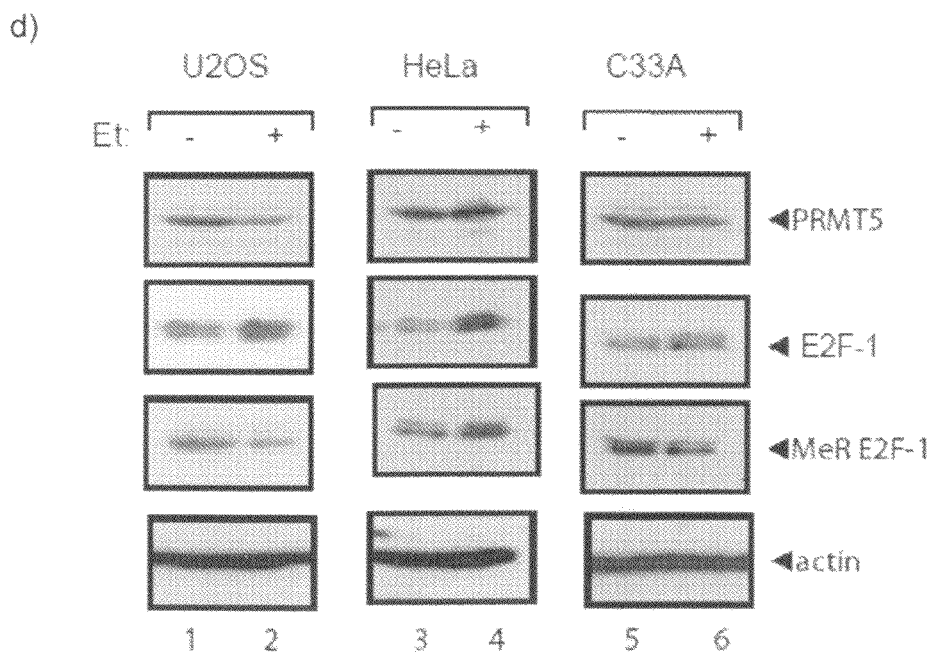

It was investigated whether E2F-1 is methylated in cells using a site-specific methylated-arginine peptide antibody, prepared against a methylated RGRGR peptide taken from E2F-1, in which the predominant sites of methylation, R111 and R113, were symmetrically methylated. As shown in FIG. 2a, anti-MeR-E2F-1 recognised ectopic wild-type E2F-1 immunoprecipitated from cells, but failed to react with either the KK or KKK mutants, indicating that the antibody recognised the relevant region in E2F-1. Either wild-type E2F-1, KK or KKK expression vectors were transfected to HeLa cells and immunoprecipitated (IP) with HA11, followed by immunoblotting (IB) with anti-MeR E2F-1, HA11 (E2F-1) or DP-1 antibodies. The level of input (In) protein is indicated.

The specificity of the antibody for arginine methylated E2F-1 was established by immunoprecipitating ectopic E2F-

1, followed by immunoblotting with anti-MeR-E2F-1 in the presence of competing matched E2F-1 peptides that differed only in the methylation status of R111 and R113. In FIG. 2b, either wild-type E2F-1, KK and KKK expression vectors were transfected to HeLa cells and immunoprecipitated (IP) with HA11, followed by immunoblotting with anti-MeR E2F-1 or HA11 (E2F-1), either in the presence of methylated (Me-E2F-1) or unmethylated E2F-1 peptide (1 µg), as indicated. Two different exposures (short and long) of the HA11 (E2F-1) blot are shown. Anti-MeR-E2F-1 recognised the wild-type protein, and its binding activity was competed by the methylated but not the unmodified peptide (FIG. 2b, compare tracks 6 and 10). As expected, neither the KK nor KKK mutants were recognised by the anti-MeR-E2F-1 antibody (FIG. 2b). These results establish that the anti-MeR-E2F-1 peptide antibody detects methylated E2F-1 and, further, that E2F-1 expressed ectopically in cells undergoes arginine methylation.

The anti-MeR-E2F-1 antibody was used to study the methylation of endogenous E2F-1 by immunoprecipitation of E2F-1 followed by immunoblotting with anti-MeR-E2F-1. E2F-1 was found to be methylated in different cell types, including HeLa, C33A and U2OS cells (FIG. 2c and d). In FIG. 2c, HeLa or U2OS cell lysates were harvested and immunoprecipitated (1P) with anti-E2F-1 (KH95) or control antibody, followed by immunoblotting with anti-MeR E2F-1 or anti-E2F-1 antibodies. The level of input (In) E2F-1 protein is shown.

Moreover, E2F-1 methylation was regulated upon DNA damage with etoposide (FIG. 2d). In FIG. 2d, E2F-1 arginine methylation is regulated upon DNA damage treatment. U2OS, HeLa or C33A cells were treated with etoposide (+; 10 µM for 16 h) or left untreated (−), extracts prepared and subsequently immunoblotted with anti-PRMT5, anti-E2F-1, anti-MeR E2F-1 or actin (loading control) as indicated.

Further, methylated E2F-1 was present in nuclei (FIG. 2e). In FIG. 2E, U2OS cells transfected with E2F-1 expression vector were immunostained with anti-E2F-1 or anti-MeR E2F-1 in the presence or absence of competing methylated E2F-1 peptide as indicated. DAPI shows the location of nuclei.

These results indicate that endogenous E2F-1 undergoes arginine methylation, and further show that the level of arginine methylation is regulated upon DNA damage treatment.

Example 3

The Effect of E2F-1 Methylation

Figure 3:
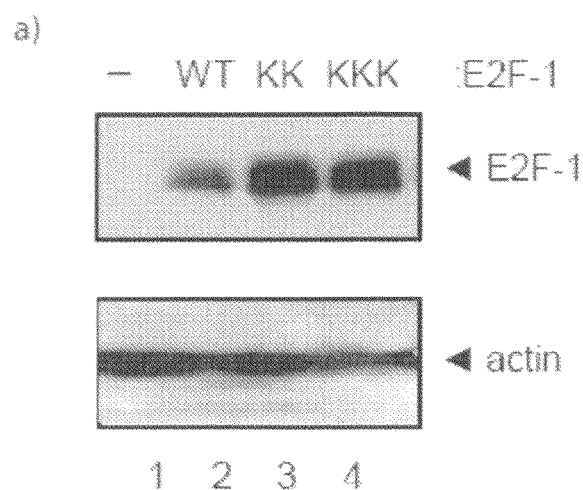
FIGS. 3a-3h show the properties of arginine methylated E2F-1.
Figure 3:
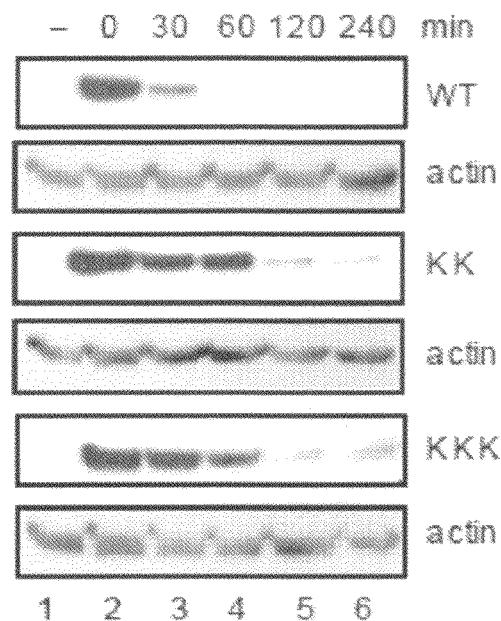
Figure 3:
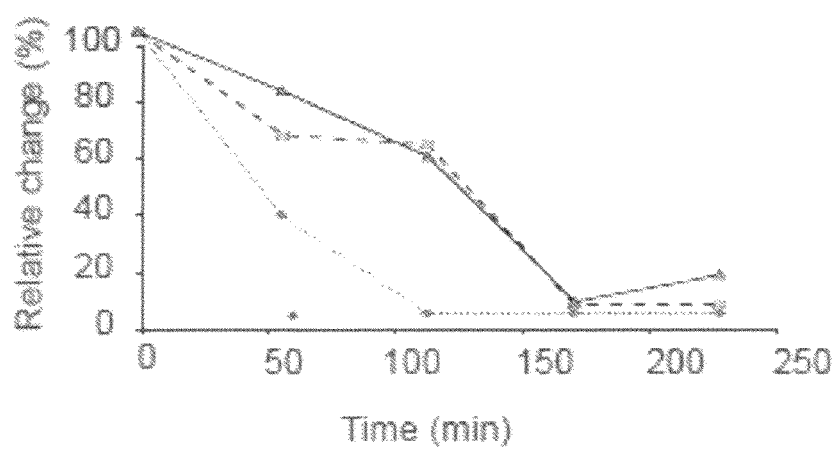
Figure 3:
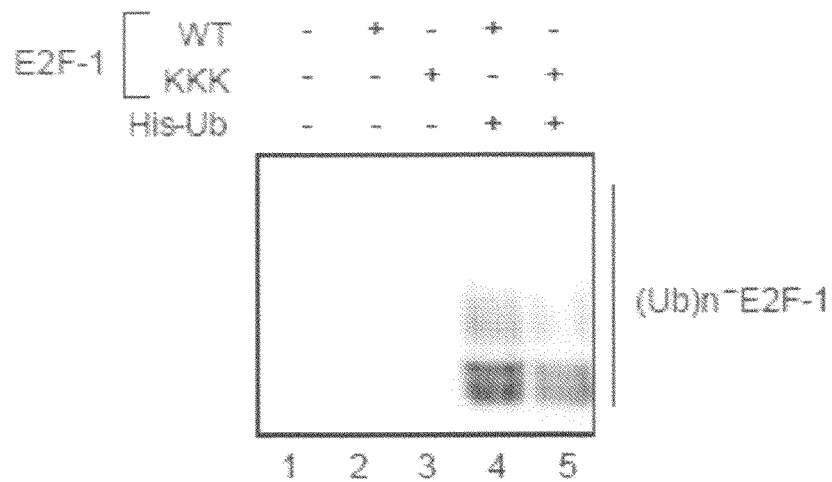
Figure 3:
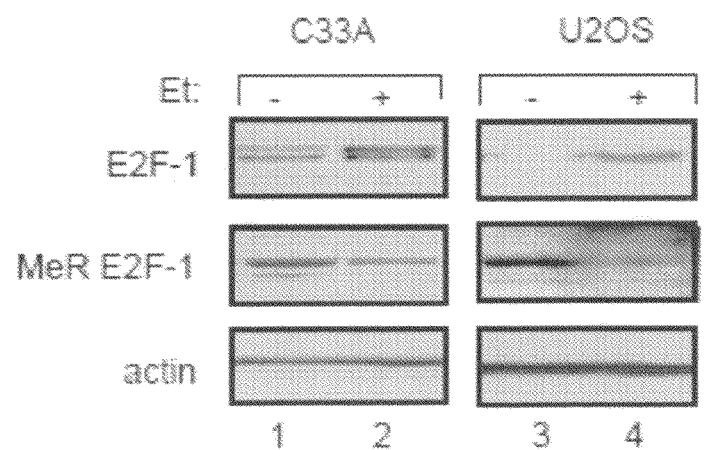

Since arginine methylation of E2F-1 is regulated by DNA damage, and because E2F-1 is induced upon DNA damage (Stevens and La Thangue 2003; Iaquinta and Lees 2007; Polager and Ginsberg 2008), it was considered that arginine methylation may play a role in the controlling E2F-1 stability. When the level of ectopic protein was compared, both the KK and KKK mutants were expressed at increased levels compared to wild-type E2F-1. FIG. 3a shows the levels of wild-type E2F-1, KK and KKK after transfection (1 µg) into U2OS cells. '-' in the left lane indicates untransfected cells. In part, this difference reflected their altered protein stability, because each of the KK and KKK mutants exhibited an increased half-life compared to wild-type E2F-1. FIG. 3b shows the stability of wild-type E2F-1, KK and KKK mutants. Expression vectors (1 µg) encoding wild-type E2F-1 (WT), KK and KKK mutants were transfected into U2OS cells for 48 h. Cells were treated with 100 µg/ml of cyclohexamide, and then harvested at 0, 2 h, 4 h, 6 h post treatment time points as indicated for subsequent immunoblotting (i), and further quantitated (ii). The HA11 antibody was used for immunoblotting and actin served as protein loading control; n=2. Both the KKK (solid line) and KK (dashed line) mutants had similarly increased half-life compared to wild-type (dotted line) E2F-1 (75 to 25 min respectively). These results suggest that arginine methylation of E2F-1 negatively regulates protein stability.

To explore this possibility in greater detail and establish whether PRMT5 had a direct effect on E2F-1, PRMT5 in cells was depleted using siRNA and thereafter measured E2F-1 protein levels. The depletion of PRMT5 co-incided with increased levels of E2F-1 protein (FIG. 3c), which is compatible with the increased level and stability of the KK and KKK mutants (FIG. 3b). FIG. 3c shows that PRMT5 siRNA increases E2F-1 protein levels. PRMT5 (P) or control (C) non-targeting siRNA was transfected into U2OS cells, and cells harvested 72 h post transfection with or without etoposide treatment (10 µM) in the last 16 h. Extracts were immunoblotted with anti-PRMT5 and E2F-1, and GAPDH levels served as a loading control.

Further, E2F-1 RNA was higher under conditions of PRMT5 depletion, contrasting with the control siRNA treatment. FIG. 3d shows E2F-1 RNA levels in PRMT5 siRNA treated cells. RNA was extracted from cells treated as described above, and RNA levels of E2F-1 examined. RNA levels of 18S and GAPDH served as controls. This result might reflect the ability of E2F-1 protein to positively auto-regulate expression of the E2F-1 gene (Stevens and La Thangue 2003). Significantly, under conditions of PRMT5 depletion and the consequent increased E2F-1 levels, a variety of E2F target genes were induced, including p73, Chk1 and Chk2 and Cdc2. FIG. 3E shows protein levels of E2F-1 target genes in PRMT5 siRNA treated cells. PRMT5 (P) or control (C) non-targeting siRNA was transfected into U2OS cells and cells were harvested 72 h post transfection with or without etoposide (Et; 10 µM) or doxorubicin (Dox; 2 µM) treatment in the last 16 h. Extracts were immunoblotted with anti-PRMT5, E2F-1, p73, Chk2, Chk1 and Cdc2 as indicated. Levels of GAPDH served as the loading control.

These results suggest therefore that arginine methylation regulates E2F-1 protein levels, which in turn impacts on the expression of downstream E2F target genes.

FIGS. 3f and g show that PRMT5 regulates the ubiquitination of E2F1. FIG. 3f shows the ubiquitination of wild-type E2F-1 and the KKK mutant. H1299 cells were transiently transfected with expression vectors encoding wild-type (WT) E2F-1 or KKK (2 µg), together with His6-ubiquitin (4 µg) as indicated. Cells were treated with MG132 (20 nM) for 4 h before harvesting. Cell lysates and Ni2+ pull-down eluates were analysed as described. The KKK E2F1 mutant (which cannot be methylated) is ubiquitinated at a lower level that WT E2F1, which explains its increased stability upon PRMT5 knockdown (see FIG. 3c).

FIG. 3g shows the effect of PRMT5 on E2F-1 ubiquitination. U2OS cells were transfected with PRMT5 (P) or control (C) siRNA. After 24 h, cells were transfected with expression vectors encoding wild-type (WT) E2F-1 or the KKK mutant (2 µg) and His 6-ubiquitin (4 µg) as indicated. Cells were treated with MG132 (20 nM) for 4 h before being collected. Cell lysates and Ni2+ pull-down eluates were analysed as described. Quantitation of ubiquitin signals was performed using ImageJ 1.43u, and the input protein levels are shown underneath. It can be seen that PRMT5 knockdown affects the ubiquitination of E2F-1 (compare lanes 2 to 4).

FIG. 3h shows that E2F-1 arginine methylation is regulated upon DNA damage treatment. C33A or U2OS cells were treated with etoposide (Et+; 10 µM for 16 h) or left untreated (−), extracts prepared and subsequently immunoblotted with anti-E2F-1, anti-MeR E2F-1 or actin (loading control) as indicated. FIG. 3*h* shows that in cancer cells grown in vitro, changes in E2F-1 protein levels coincide with changes in arginine methylation of E2F-1. Thus, the top blot shows overall levels of E2F-1, and the middle blot (MeR E2F-1) the level of methylated E2F-1 (note the inverse correlation).

Example 4

Functional Consequences of Arginine Methylation

Figure 4:
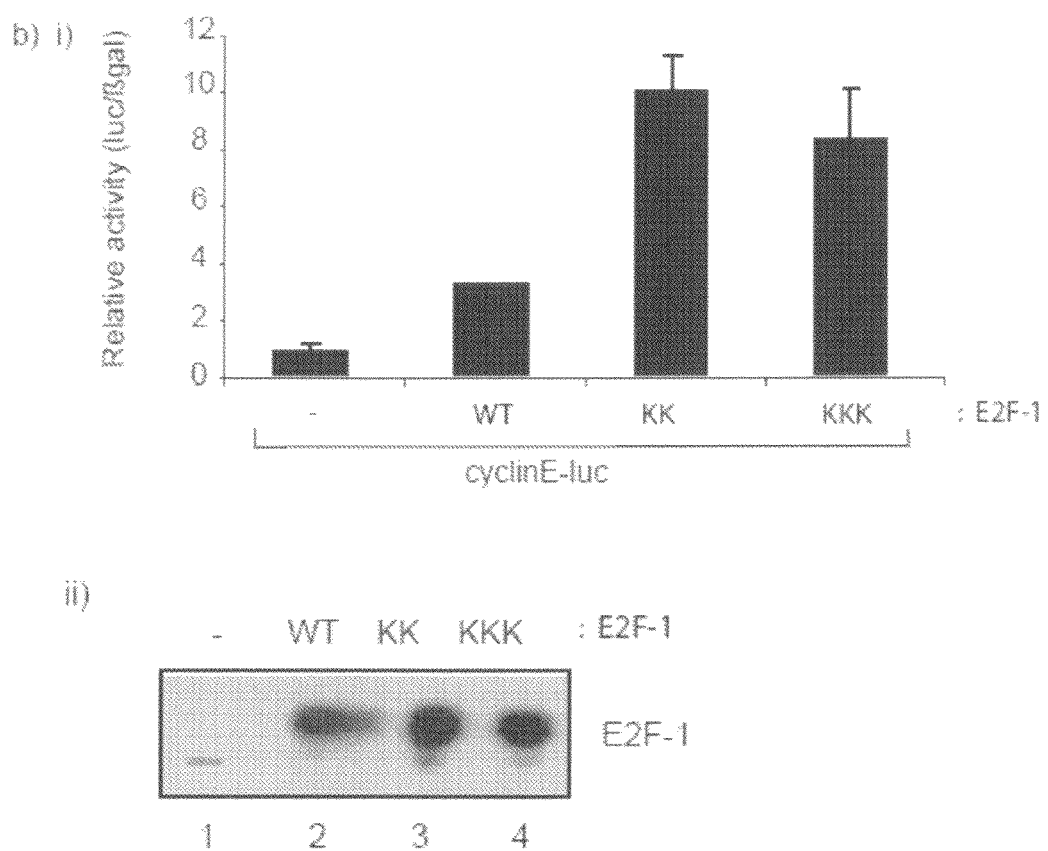
FIGS. 4a-4g show the functional properties of arginine methylated E2F-1.
Figure 4:
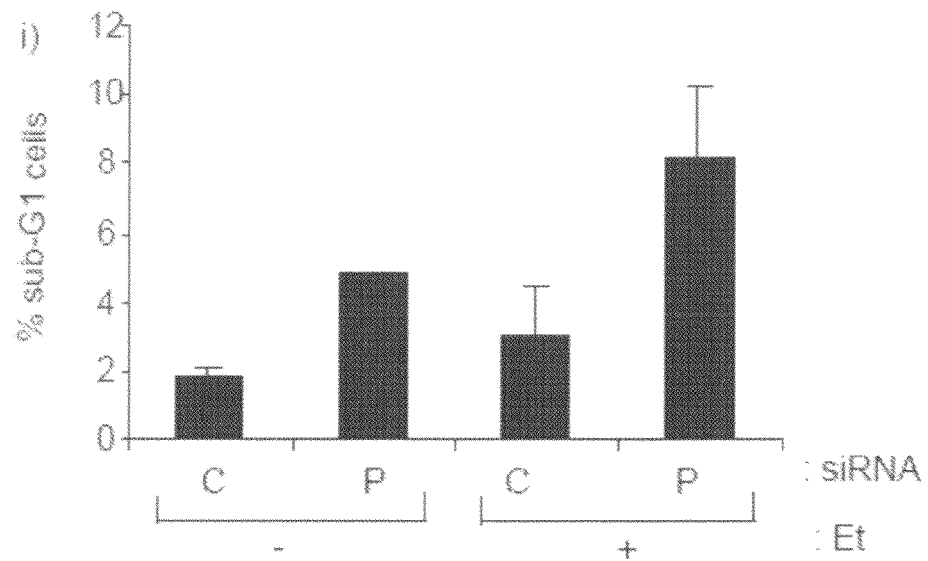
Figure 4:
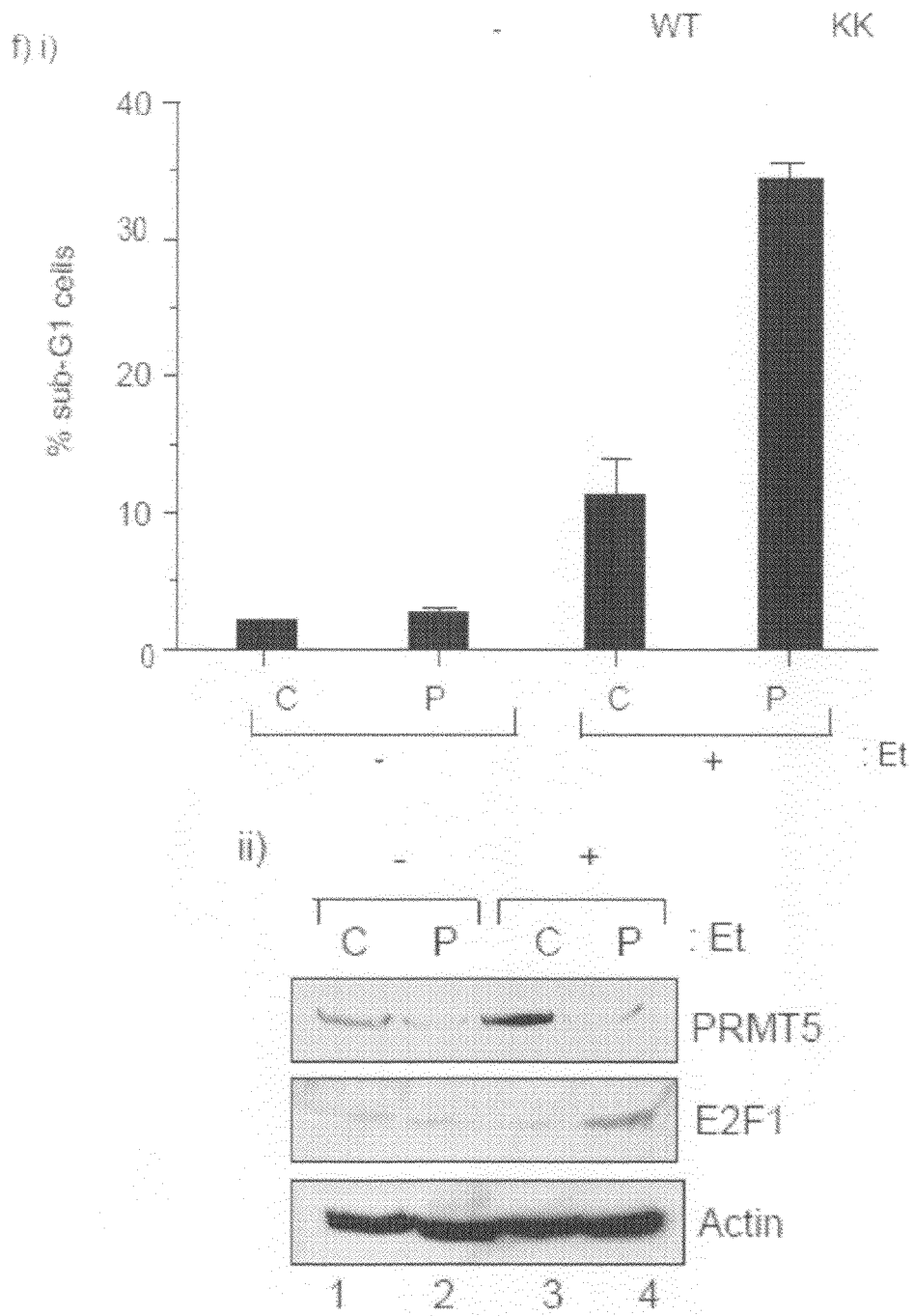
Figure 4:
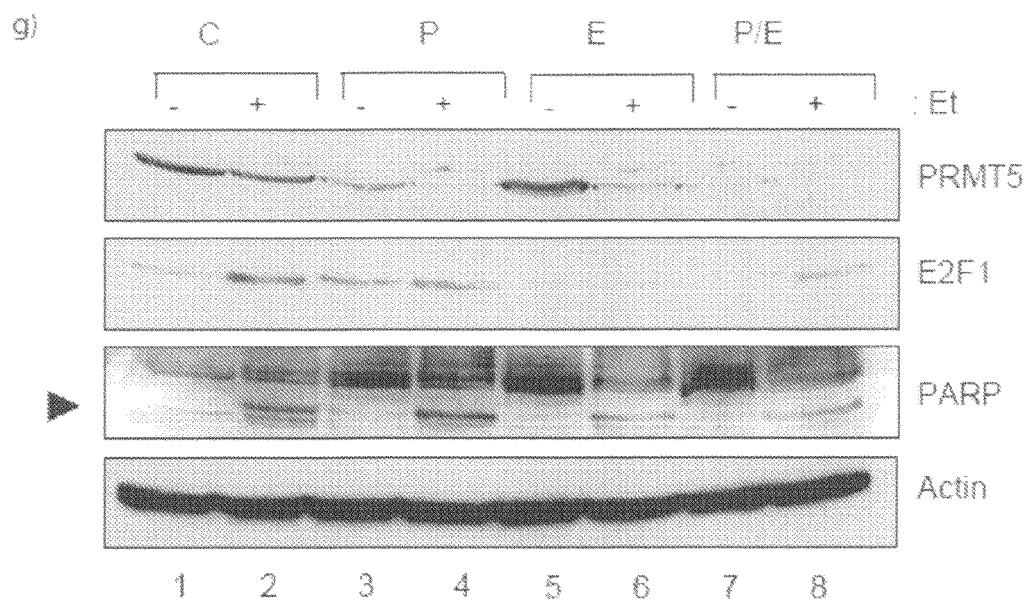

To further explore the role of arginine methylation in the transcription properties of E2F-1, wild-type E2F-1 was compared with the KK and KKK mutants in a reporter-based transfection assay, using E2F-responsive promoters derived from E2F target genes. The assay was performed under conditions in which each mutant protein was expressed at an equivalent level to wild-type E2F-1 (FIG. 4*aii* and *bii*), thus ruling out any difference in activity that could be attributed to protein levels. Under these conditions, both the KK and KKK mutants exhibited increased transcriptional activity compared to wild-type E2F-1. FIGS. 4*a* and *b* show the transcription properties of wild-type E2F-1, KK and KKK mutants. U2OS cells were transfected with expression vectors encoding WT or mutant E2F-1 protein, together with p73-luciferase (A) or cyclinE-luciferase (B) for 48 h as indicated, and pCMV-βgal to monitor transfection efficiency. Relative luciferase activity (luciferase/βgal) is shown together with expression level of ectopic proteins; n=3. These results suggest therefore that arginine methylation impacts on the ability of E2F-1 to activate transcription, and explains in part the increased expression of E2F target genes under conditions of PRMT5 depletion. Furthermore, under conditions of PRMT5 depletion through treatment with siRNA, E2F-1 responsive promoters were more active (FIG. 4*c*). FIG. 4*c* shows E2F transcription upon PRMT5 depletion. PRMT5 (P) or control (C) non-targeting siRNA was transfected into U2OS cells together with p73-luciferase (i) or cyclinE-luciferase (ii) for 48 h, together with pCMV-βgal to monitor transfection efficiency. Relative luciferase activity is shown together with expression level of the ectopic proteins.

Example 5

Arginine Methylation Regulates Apoptosis

Whether arginine methylation influences E2F-1-dependent apoptosis was investigated by comparing the ability of wild-type E2F-1 to the KK and KKK mutants to induce cells with a sub-G1 DNA content (Stevens et al 2003). When each protein was compared, both mutants exhibited increased levels of apoptosis relative to wild-type E2F-1. FIG. 4*d* shows apoptosis induced by wild-type E2F-1, KK and KKK mutants. U2OS cells were transfected with expression vectors encoding wild-type E2F-1, KK and KKK as indicated for 48 h and analysed by FACS as described. The graph represents the relative change in sub-G1 populations compared to the empty vector control treatment; n=2.

Moreover, an increased level of apoptosis was also apparent when PRMT5 was depleted through siRNA in different cell types, in both unperturbed and DNA damaged cells. FIG. 4*e* shows apoptosis upon PRMT5 depletion. PRMT5 (P) or control (C) non-targeting siRNA was transfected into U2OS cells and the cells were harvested 72 h post-transfection (with or without etoposide (10 µM) for 16 h) and analysed by FACS. The graph (i) represents the relative number of sub-G I cells (compared to the control treatment) in the indicated conditions; and (ii) the level of PRMT5 and E2F-1; n=3. FIG. 4*f* shows apoptosis upon PRMT5 depletion in C33A cells (i) and levels of PRMT5 and E2F-1 (ii).

Most importantly, the increased level of apoptosis seen upon PRMT5 depletion was dependent on E2F-1 activity, because in conditions where E2F-1 was compromised through treatment with E2F-1 siRNA, the level of apoptosis upon PRMT5 depletion was much less. FIG. 4*g* shows that apoptosis upon PRMT5 depletion is dependent upon E2F-1. PRMT5 (P), E2F-1 (E) or control (C) siRNA was transfected into C33A cells as indicated, with or without etoposide treatment, and the level of PARP cleavage, reflecting apoptosis, measured. Cleaved PARP is indicated by the arrow. These results indicate that arginine methylation regulates the apoptotic properties of E2F-1, and that the apoptosis induced upon PRMT5 depletion is dependent upon E2F-1.

The results presented here show that PRMT5 can influence E2F-1-dependent apoptosis, and identify the arginine residues in E2F-1 which are modified by PRMT5. Because E2F-1 mutants that are compromised in methylation exhibited heightened apoptotic activity, our results argue that arginine methylation acts to negatively regulate apoptosis. It is consistent with a role for arginine methylation in regulating apoptosis that depleting PRMT5 in cells caused a co-incident increase in apoptosis. However, the enhanced apoptosis activity not only reflected increased E2F-1 protein levels, but also altered functional properties. For example, when expressed at equivalent protein levels, both the KK and KKK mutants, which are devoid of arginine methylation, possessed increased activity. Arginine methylation therefore regulates a number of different properties in E2F-1, which have the combined effect to regulate E2F-1-dependent apoptosis.

Figure 5:
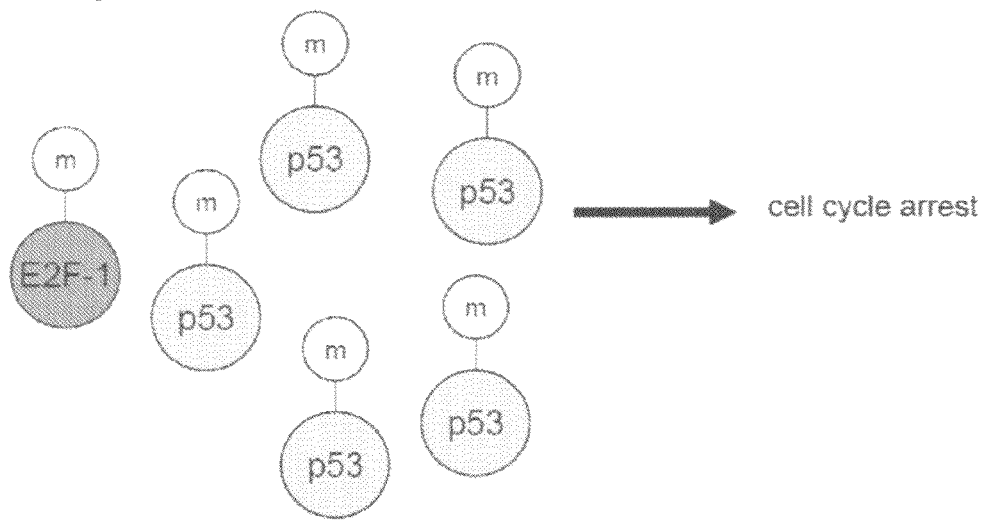
FIG. 5 shows a model for arginine methylation in E2F-1 control.
Figure 5:
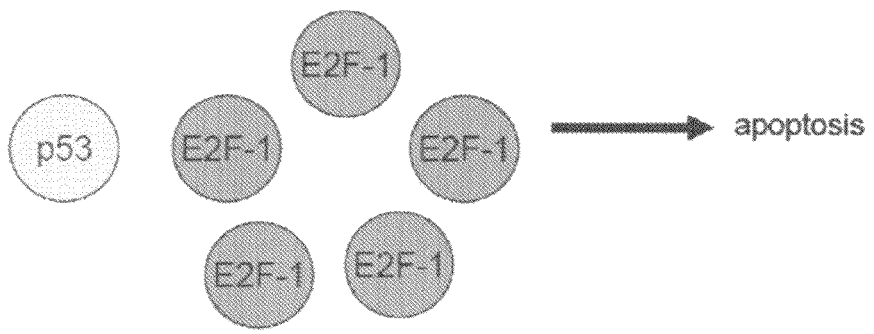

Arginine methylation targets the p53 protein, and impacts on the physiological outcome of the p53 response (Jansson et al 2008). That arginine methylation of p53 prompts cell cycle arrest, rather than apoptosis (Jansson et al 2008), is compatible with the observations described herein. Namely, as shown in FIG. 5, when E2F-1 is methylated, its apoptotic activity is held in check (through for example low protein levels and reduced expression of target genes), allowing arginine methylated p53 to over-ride E2F-1 and prompt cell cycle arrest. In contrast, under conditions that limit arginine methylation (for example PRMT5 siRNA), E2F-1 levels and apoptotic activity increase, which over-rides the cell cycle arrest activity imposed by p53. Arginine methylation therefore allows a critical level of interplay to occur between the pathways controlled by E2F-1 and p53. By enabling crosstalk between E2F-1 and p53, arginine methylation is able to control a key decision point, dictating whether apoptosis or cell cycle arrest is the predominant outcome. Arginine methylation therefore provides a signal, and PRMT5 the mechanism, through which E2F-1 and p53 activity is integrated.

Example 6

Arginine Methylation and Apoptosis

In this example the effect of manipulating the levels of PRMT5 in cells on apoptosis was examined, as was the effect of co-manipulating E2F-1.

Figure 6:
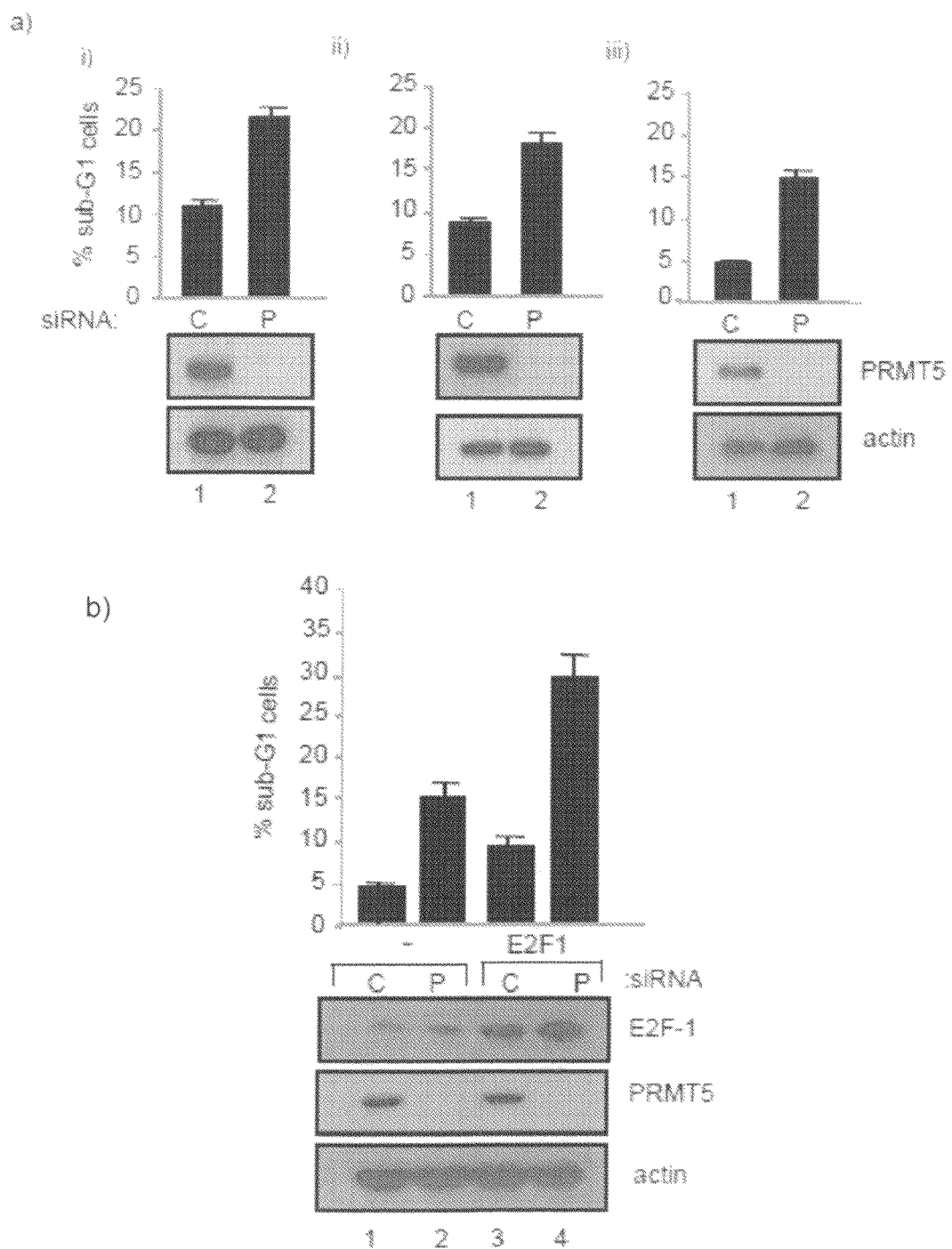
FIGS. 6a-6g show that PRMT5 regulates apoptosis by suppressing E2F-1.
Figure 6:
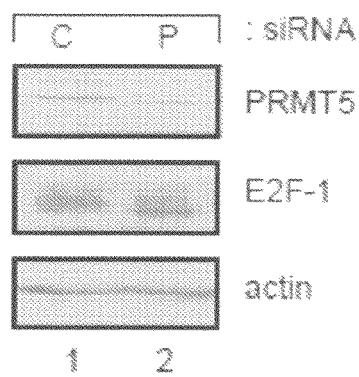
Figure 6:
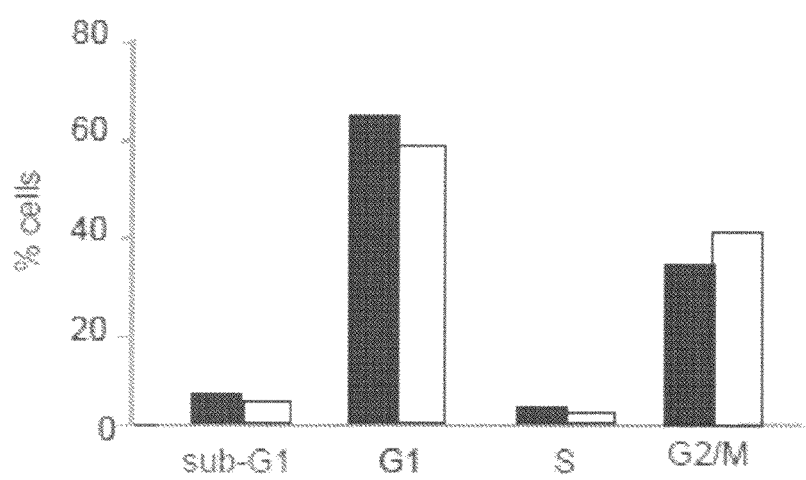
Figure 6:
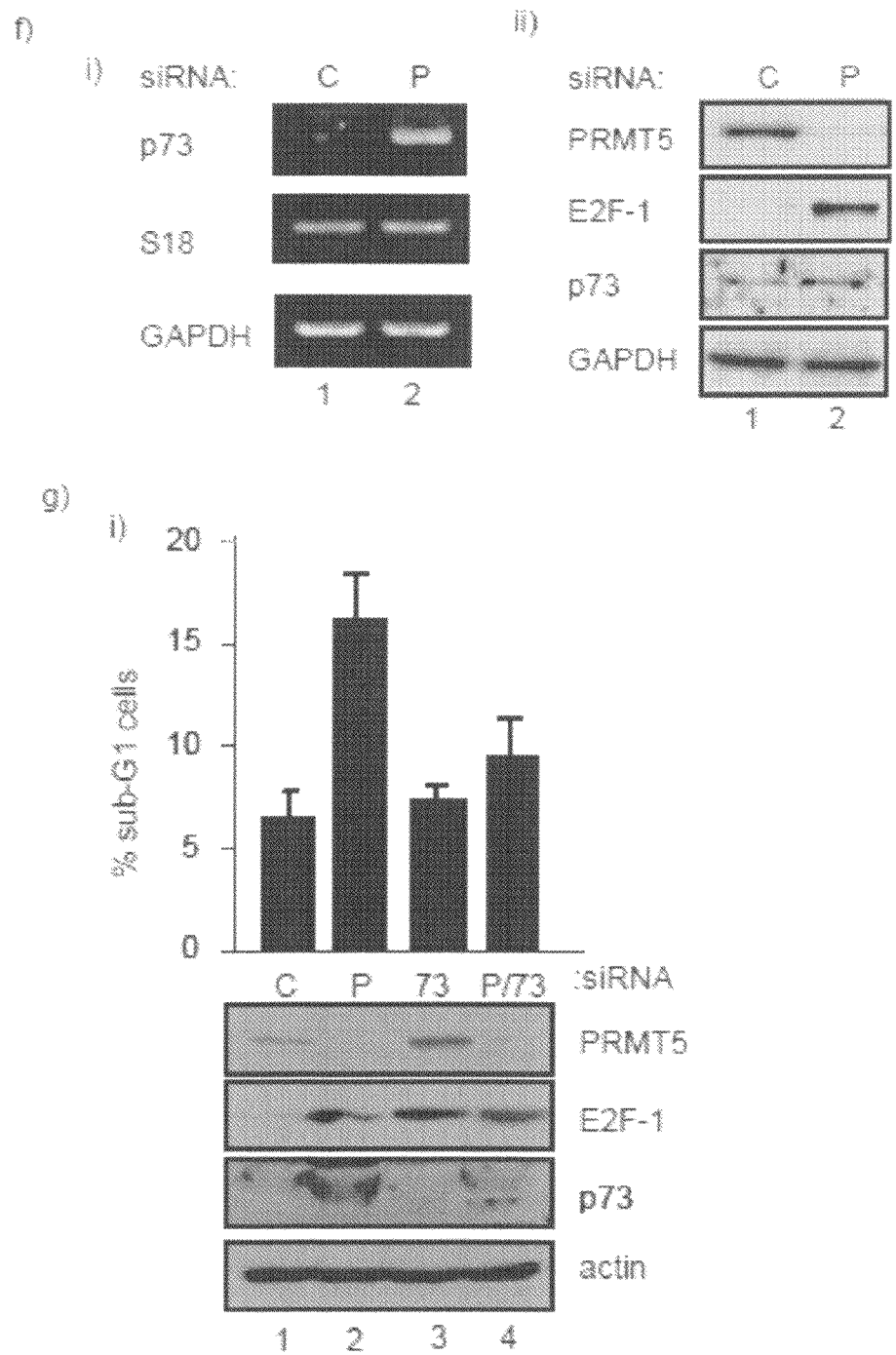

FIG. 6*a* shows apoptosis upon PRMT5 depletion. PRMT5 (P) or control (C) non-targeting siRNA (25 nM) was transfected into HCT116 p53+/+ (i), HCT116 p53−/− (ii) or U2OS (iii) cells and the cells were harvested 72 h post-transfection and analysed by FACS. The graph represents the actual number of sub-G1 cells in the indicated conditions, and the immunoblot the level of PRMT5 and actin control; n=3. It can be seen that depleting PRMT5 in a variety of tumour cells (independent of p53 status) induces apoptosis (top graph % sub-G1 cells).

FIG. 6b shows apoptosis upon PRMT5 depletion. PRMT5 (P) or control (C) non-targeting siRNA was transfected into SAOS2 together with an expression vector encoding wild-type E2F-1 (1 µg) as indicated, harvested at 72 h and processed as described in (a); n=3. It can be seen that depleting PRMT5 causes enhanced levels of apoptosis in the presence of ectopic E2F-1. This is consistent with the idea that PRMT5 mediates its effects through E2F-1.

FIG. 6c shows the effect of PRMT5 siRNA in MEFs. PRMT5 (P) or control (C) non-targeting siRNA was transfected into MEFs and cells harvested at 72 h post-transfection as indicated. Cell extracts were immunoblotted with anti-PRMT5 and anti-E2F-1. Actin levels served as the loading control.

MEFs were treated as described in 6c and thereafter analysed by FACS. In FIG. 6d the black bar represents the effect of C siRNA, and clear bar the effect of P siRNA; n=3. FIGS. 6c and 6d show that increased apoptosis does not occur in normal non-cancer cells because no apoptosis in MEFs.

FIG. 6e shows apoptosis upon PRMT5 and E2F-1 depletion. PRMT5 (P), E2F-1 (E) or control (C) non-targeting siRNA was transfected into U2OS cells and harvested 72 h post-transfection and analysed by FACS as described. The graph shows the level of sub-G1 cells compared to the control treatment and the level of endogenous PRMT5 and E2F-1 is shown underneath; n=3. It can be seen that the co-depletion of PRMT5 and E2F-1 (P/E in the figure) prevents the induction of apoptosis, in contrast to PRMT5 depletion alone, i.e. the induced apoptosis is mediated through E2F1 activity.

FIGS. 6f and 6g address the role of one of the key E2F target genes in the PRMT5 dependent apoptosis, i.e. p73. FIG. 6f shows the effect of PRMT5 siRNA on p73. PRMT5 (P) or control (C) siRNA was transfected into U2OS cells and cells harvested at 72 h post-transfection. Both RNA (i) and protein (ii) levels were measured, as indicated, for p73, 18S and GAPDH (i) and PRMT5, E2F-1, p73 and GAPDH (ii). FIG. 6f shows that p73 is upregulated upon PRMT5 knockdown (both RNA and protein) and that p73 activity is also required for the apoptosis that occurs upon PRMT5 knockdown. This experiment supports activation of the E2F1 pathway leading to apoptosis upon PRMT5 knockdown, i.e. PRMT5 normally acts to suppress activation of the pathway.

FIG. 6g shows apoptosis upon PRMT5 and p73 depletion. PRMT5 (P), p73 (73) or control (C) non-targeting siRNA was transfected into U2OS cells and harvested at 72 h post-transfection and analysed by FACS. The graph represents the relative change in the sub-G1 population compared to the control treatment, and the level of PRMT5, E2F-1 and p73 is shown underneath; n=3.

Example 7

PRMT5 and E2F-1 Expression in Clinical Tumour Biopsies

FIG. 7a shows representative images of PRMT5 and E2F-1 IHC in an MDA-MB-23I breast cancer cell xenograft showing examples of E2F-1 and PRMT5 staining cells. Note that both positive and negative E2F-1 and PRMT5 stained tumour cells are evident (indicated by arrows; 20× and 40× magnification, as indicated).

FIG. 7b shows representative images of PRMT5 and E2F-1 IHC in human mantle cell lymphoma biopsy showing areas of PRMT5 positive and E2F-1 negative tumour cells.

Note that the expression level of E2F-1 was considerably less that PRMT5 in the lymphoma sections.

FIG. 7c shows representative images of PRMT5 IHC in follicular lymphoma. The follicles containing malignant cells which stain intensely with anti-PRMT5 are indicated (i), and at higher magnification in (ii).

FIGS. 7d and 7e show representative images of PRMT5 and E2F-1 IHC in CRC. Examples of tumours expressing low PRMT5/high E2F-1 (d) and high PRMT5/low E2F-1 (e), and are shown, together with fields of increased magnification. The images in FIGS. 7d and 7e show that tumours do exist with either high PRMT5/low E2F1 versus low PRMT5/high E2F1. The present invention is particularly concerned with treating tumours with high PRMT5/low E2F1 with a PRMT5 inhibitor, in order to inactivate PRMT5 and thereby activate E2F1.

MATERIALS & METHODS

Cell Culture

U2OS, C33A, MCF7, HCT116, SAOS2, HeLa, H1299 cells and MEFs were maintained in DMEM with 5% FCS.

Antibodies

The following antibodies were used; anti-Flag peptide monoclonal antibody M2 (Sigma), anti-Flag peptide monoclonal antibody M2 coupled agarose beads (Sigma), and anti-HA11 monoclonal antibody (Covance). PRMT5 antibody was from Upstate. GST, E2F1, Chk1, Cdc2 and p53 antibodies were monoclonal antibodies from Santa Cruz. DP-1, p73, Chk2 and GAPDH were polyclonal antibodies from Santa Cruz. β-actin monoclonal antibody was from Sigma. PARP monoclonal antibody was from BD Pharmingen.

Transfection

Gene Juice transfection reagent (Novagen, San Diego, Calif.) was used to transfect cells with DNA. All transfections with the indicated plasmids included a pCMV-βGal internal control for gauging transfection efficiency. Empty pcDNA3.1a vector was used to equalise amounts of transfected DNA where appropriate.

siRNA

Oligofectamine transfection reagent (Invitrogen) was used to transfect cells with siRNAs for 72 h. siRNA treatment of cells was carried out using siRNA non-targeting (Dharmacon) as control or PRMT5 (5' CCGCUAUUGCACCUUG-GAA (SEQ ID NO:1)). p73 smart pool siRNA was from Dharmacon. siRNA treatment was for 72 h at 50 nM.

Flow Cytometry

Cells were transfected with the indicated expression vectors together with pBB14-GFP (for 48 h) to monitor transfection efficiency or siRNA (for 48 h or 72 h) with or without treatment of the DNA damage agent for the last 16 h. Then, cells were fixed and stained with propidium iodide and analyzed by Flow Cytometry.

Reporter Assay

Cells were transfected with expression vectors (1 µg) encoding WT or the mutant E2F-1 proteins as indicated with E2F responsive luciferase reporters, namely p73-luciferase or cyclinE-luciferase, together with pCMV-βgal to monitor transfection efficiency. Cells were harvested, lysed 48 h post-transfection and luciferase activity measured as previously described (Janson et al 2008).

Chromatin Immunoprecipitation

U2OS cells were maintained in DMEM containing 5% foetal calf serum. Cells were transfected with 50 nM PRMT5 siRNA or a non-targeting control (C) siRNA for 72 h. Cells were cross-linked with formaldehyde (final concentration 1%). Chromatin was prepared as described previously (Zalmas et al., 2008). Antibodies used for immunoprecipitation were as follows: anti-E2F-1 (C-20, Santa Cruz Biotechnology), and anti-acetyl-histone H3 (Millipore). The non-specific rabbit IgG used as a negative control in the ChIP assays was from Jackson ImmunoResearch. The recovered DNA was analyzed by semi-quantitative PCR. Primer sequences are available upon request.

Cyclohexamide Half-Life Assay

Cells were transfected with WT or mutant HA-E2F1 plasmids for 48 h as indicated. Cells were treated with 100 ug/ml of cyclohexamide (Fluka) and then harvested at different time points as indicated for immunoblotting.

Preparation of Whole Cell Extracts, Immunoprecipitation and Immunoblot Analysis

Cells were either left untransfected or transfected with expression vectors as indicated. At 48 h post transfection, cells were harvested in TNN buffer (50 mM Tris-HC1 [pH 7.4], 150 mM NaCl, 5 mM EDTA, 0.5% Ipegal, 50 mM NaF, 0.2 mM sodium orthovanadate and protease inhibitor cocktail (1 mM PMSF, leupeptin [1 µg/ml], aprotinin [1 µg/m1], and pepstatin A [1 µg/ml])) and rotated at 4° C. for 30 min to 1 h. The cell lysate was then homogenised, centrifuged at 11000 rpm for 10 min to remove cell debris and the supernatant collected. All lysates were normalized for protein concentration and, where appropriate, for transfection by β-galactosidase activity. Immunoprecipition was carried out by incubation of lysates with the indicated antibody and protein-A/G Sepharose beads or agarose-antibody conjugated at 4° C. for 4 h or overnight. The beads were collected and washed three times with TNN buffer (containing 0.25 mg/ml Ipegal) before denaturation and SDS-PAGE. Protein was transferred to nitrocellulose and probed with the indicated antibody. Enhanced chemi-luminescence (Pierce Biotechnology, Rockford, Ill.) was used to visualize antibody binding.

Ubiquitination Assays

Cells were transfected with pcDNA3.1a-ubiquitin (His-tagged) and treated as described. Briefly cells were harvested into 8 M urea, 0.1 M Na$_2$HPO$_4$/NaH$_2$PO$_4$, 0.01 M Tris-HCl, and pH 8.0. Cell lysate was incubated with nickel (Ni$^{2+}$-NTA)-agarose beads (Qiagen), 5 mM imidazole and 10 mM β-mercapthoethanol overnight at 4° C. The beads were collected and washed as described (Liu and Warbrick, 2006). Bound proteins were then eluted and assayed by immunoblotting.

Site-Directed Mutagenesis

The following primers were used: 5'-GAGCAGTGGGC-CAGCTAAAGGCAGAGGCCGCC-3' (SEQ ID NO:8) and 5'-GGCGGCCTCTGCCTTTAGCTGGCCCACTGCTC-3' (SEQ ID NO:9) were used for making mutant E2F-1 R109K. 5'-AGCTCGGGGCAAAGGCCGCCATC-3' (SEQ ID NO:10) was used for making mutant E2F-1 R111K. 5'-GGGCAGAGGCAAACATCCAGGAA-3' (SEQ ID NO:11) was used for making mutant E2F-1 R113K. 5'-AGTGGGCCAGCTCGGGGCAAAGGCAAA-CATCCAGGAAAAGGTGTG-3' (SEQ ID NO:12) was used for making mutant E2F-1 KK. 5'-AGAGCAGTGGGC-CAGCTAAGGGCAAGGGCAAGCATCCAG-GAAAAGGTGTG-3' (SEQ ID NO:13) was used for making mutant E2F-1 KKK. Quick Change Mutagenesis Kit (Stratagene) was used.

Purification of GST-E2F1 Fusion Proteins

Wild-type GST-E2F1 and the GST-E2F1 mutants were expressed in *E. coli* BL2'-DE3 (Stratagene) cells by induction with isopropyl β-D-1-thiogalactopyranoside (IPTG) (0.1 mM). Cell pellets resuspended in lysis buffer consisting of phosphate buffered saline containing protease inhibitor cocktail (1 mM PMSF, leupeptin [1 µg/ml], aprotinin [1 µg/ml], and pepstatin A [1 µg/ml]) were sonicated. 1% Triton-X100 was then added and the cells lysed at 4° C. for 30 min. Following centrifugation at 13,000 rpm for 30 min the supernatants were incubated with glutathione affinity resin (Pharmacia) for 2 h at 4° C. The beads were then washed three times with lysis buffer containing 0.1% Triton-X100, once with lysis buffer without Triton-X100 and then once with elution buffer (50 mM Tris-HCl pH8, 50 mM NaCl). GST fusion proteins were eluted from the beads by using 20 mM glutathione dissolved in elution buffer.

In Vitro Methyltransferase Assays

Flag-PRMT5 plasmid was transfected into U2OS cells for 48 h. Cells were lysed and Flag-PRMT5 was immunoprecipitated with agarose beads and then eluted. The elute was mixed with recombinant substrates (GST fusion proteins or histones) in methylation reaction buffer (50 mM Tris, 0.1 mM EDTA, 50 mM NaCl) with $^3$H labeled SAM (as —CH$_3$ group donor) to a volume of 40 µl and incubated at 30° C. for 90 min. Half of the reactions were then spotted onto p81 membrane circles (Whatman) and air dried. The membranes were then washed three times, 5 min each in 50 ml of wash buffer (46 mM NaHCO$_3$, 4 mM Na$_2$CO$_3$, pH 9.2). After washing briefly with acetone, membranes were air dried, placed in scintillation vials, immersed in scintillation fluid (Beckman Coulter) and disintegrations per minute (DPM) measured in a scintillation counter. The other half of the reactions were run on SDS-PAGE gel and used to detect $^3$H auto-radioisotope/methylation signal.

GST Binding Assay

GST or GST tagged proteins (10 µg each) were incubated with agarose beads and damaged or undamaged U2OS cell lysates for 3 h. Beads were then washed with TNN buffer 3 times. SDS sample buffer was added to beads and samples were analysed by immunoblotting.

Preparation and purification of anti-MeR E2F-1 antibody

The E2F-1 peptides, either unmethylated (CESSGPARGR-GRHPGKG (SEQ ID NO:7)) or with R111 and 8113 symmetrically methylated (sequence) (CESSGPARGR(Me)GR(Me)HPGKG (SEQ ID NO:6)), were injected into rabbits for antibody preparation (Alta Bioscience). At the appropriate time, rabbit serum diluted in PBS was purified by peptide affinity chromatography as described (Jansson et al 2008).

Histopathology

Paraffin-embedded formalin-fixed tissue from different tumour types were cleared of paraffin in Citroclear, and rehydrated through graded alcohol baths. After a rinse in water, sections were heated at 95° C. for 20 min in 10 mM sodium citrate, pH 6 for antigen retrieval. Slides were incubated in 0.5% hydrogen peroxide for 15 min to inactivate endogenous peroxidases. Slides were washed in phosphate buffered saline/0.1% Tween 20 (PBST) for 5 min before being blocked in serum for 20 min. Slides were incubated in primary antibodies; anti-PRMT5 or anti-E2F-1 overnight at 4° C. This was followed by corresponding anti-HRP secondary antibodies, ABC reagent (Vectorlabs) and then substrate (DAB; Vectorlabs). Slides were placed in hematoxylin (Sigma) for 5s for nuclear counterstaining and then mounted with coverslips using AquaTex (Merck). Sections were examined under a light microscope.

REFERENCES

Bandara, L. R. and La Thangue, N. B. 1991. Adenovirus E1a prevents the retinoblastoma protein from complexing with a cellular transcription factor. Nature 351, 494-497.

Bedford, M. T., and Richard, S. (2005). Arginine methylation an emerging regulator of protein function. Mol Cell 18, 263-272.

Bernards R, Brummelkamp T R, Beijersbergen R L. shRNA libraries and their use in cancer genetics. Nat. Methods. 2006 September; 3(9):701-6.

Botz, J., Zerfass-Thome, K., Spitkovsky, D., Delius, H., Vogt, B., Eilers, M., Hatzigeorgiou, A., and Jansen-Durr, P. (1996). Cell cycle regulation of the murine cyclin E gene depends on an E2F binding site in the promoter. Mol Cell Biol 16, 3401-3409.

Branscombe, T. L., Frankel, A., Lee, J. H., Cook, J. R., Yang, Z., Pestka, S., and Clarke, S. (2001). PRMT5 (Janus kinase-binding protein 1) catalyzes the formation of symmetric dimethylarginine residues in proteins. J Biol Chem 276, 32971-32976.

Classon, M., and Harlow, E. (2002). The retinoblastoma tumour suppressor in development and cancer. Nat Rev Cancer 2, 910-917.

Coutts, A. S., Boulahbel, H., Graham, A., and La Thangue, N. B. (2007). Mdm2 targets the p53 transcription cofactor JMY for degradation. EMBO Rep 8, 84-90.

DeGregori J (2005) E2F and cell survival: context really is key. Dev Cell 9(4): 442-444

Demonacos, C., Krstic-Demonacos, M., and La Thangue, N. B. (2001). A TPR motif cofactor contributes to p300 activity in the p53 response. Mol Cell 8, 71-84.

Demonacos, C., Krstic-Demonacos, M., Smith, L., Xu, D., O'Connor, D. P., Jansson, M., and La Thangue, N. B. (2004). A new effector pathway links ATM kinase with the DNA damage response. Nat Cell Biol 6, 968-976.

Field S J, Tsai F Y, Kuo F, Zubiaga A M, Kaelin W G, Jr., Livingston D M, Orkin S H, Greenberg M E (1996) E2F-1 functions in mice to promote apoptosis and suppress proliferation. Cell 85(4): 549-561

Frolov, M. V., and Dyson, N. J. (2004). Molecular mechanisms of E2F-dependent activation and pRB-mediated repression. J Cell Sci 117, 2173-2181.

Goyal, B. R., Patel, M. M., Soni, M. K., and Bhadada, S. V. (2009). Therapeutic opportunities of small interfering RNA. Fundam Clin Pharmacol 23, 367-386.

Hajeri, P. B., and Singh, S. K. (2009). siRNAs: their potential as therapeutic agents—Part I. Designing of siRNAs. Drug Discov Today 14, 851-858.

Iaquinta P J, and Lees J A (2007) Life and death decisions by the E2F transcription factors. Curr Opin Cell Biol 19(6): 649-657

Jackson S P, Bartek J (2009). The DNA-damage response in human biology and disease. Nature 461: 1071-8.

Jansson, M., Durant, S. T., Cho, E. C., Sheahan, S., Edelmann, M., Kessler, B., and La Thangue, N. B. 2008. Arginine methylation regulates the p53 response. Nature Cell Biology 10, 1431-1439.

Markham, D., Munro, S., Soloway, J., O'Connor, D. P., and La Thangue, N. B. (2006). DNA-damage-responsive acetylation of pRb regulates binding to E2F-1. EMBO Rep 7, 192-198.

Meister, G., Eggert, C., Buhler, D., Brahms, H., Kambach, C., and Fischer, U. (2001). Methylation of Sm proteins by a complex containing PRMT5 and the putative U snRNP assembly factor pICln. Curr Biol 11, 1990-1994.

Oh, Y. K., and Park, T. G. (2009). siRNA delivery systems for cancer treatment. Adv Drug Deliv Rev 61, 850-862.

Pal, S., Vishwanath, S. N., Erdjument-Bromage, H., Tempst, P., and Sif, S. (2004). Human SWI/SNF-associated PRMT5 methylates histone H3 arginine 8 and negatively regulates expression of ST7 and NM23 tumor suppressor genes. Mol Cell Biol 24, 9630-9645.

Pediconi, N., Ianari, A., Costanzo, A., Belloni, L., Gallo, R., Cimino, L., Porcellini, A., Screpanti, I., Balsano, C., Alesse, E., et al. (2003). Differential regulation of E2F1 apoptotic target genes in response to DNA damage. Nat Cell Biol 5, 552-558.

Polager S, and Ginsberg D (2008) E2F—at the crossroads of life and death. Trends Cell Biol 18(11): 528-535

Rao D D, Vorhies J S, Senzer N, Nemunaitis J. (2009) siRNA vs. shRNA: similarities and differences. Adv Drug Deliv Rev. 2009 Jul. 25; 61(9):746-59. Epub 2009 Apr. 20.

Ren B, Cam H, Takahashi Y, Volkert T, Terragni J, Young R A, Dynlacht B D (2002) E2F integrates cell cycle progression with DNA repair, replication, and G(2)/M checkpoints: Genes Dev 16(2): 245-256

Rho, J., Choi, S., Seong, Y. R., Cho, W. K., Kim, S. H., and Im, D. S. (2001). Prmt5, which forms distinct homo-oligomers, is a member of the protein-arginine methyltransferase family. J Biol Chem 276, 11393-11401.

Shikama, N., Lee, C. W., France, S., Delavaine, L., Lyon, J., Krstic-Demonacos, M., and La Thangue, N. B. (1999). A novel cofactor for p300 that regulates the p53 response. Mol Cell 4, 365-376.

Singer O, Verma I M. Applications of lentiviral vectors for shRNA delivery and transgenesis. Curr Gene Ther. 2008 December; 8(6):483-8.

Singh, S. K., and Hajeri, P. B. (2009). siRNAs: their potential as therapeutic agents—Part II. Methods of delivery. Drug Discov Today 14, 859-865.

Stanelle, J., and Putzer, B. M. (2006). E2F1-induced apoptosis: turning killers into therapeutics. Trends Mol Med 12, 177-185.

Stevens, C., Smith, L., and La Thangue, N. B. (2003). Chia activates E2F-1 in response to DNA damage. Nat Cell Biol 5, 401-409.

Stevens, C. and La Thangue, N. B. (2003). E2F and cell cycle control: a double edged sword. Archives of Biochemistry and Biophysics 412, 157-169.

Tilesi F, Fradiani P, Socci V, Willems D, Ascenzioni F. Design and validation of siRNAs and shRNAs. Curr Opin Mol. Ther. 2009 April; 11(2):156-64.

Toudjarska and de Fougerolles (2009). Nature Biotechnology 27, 821-823

Tsai K Y, Hu Y, Macleod K F, Crowley D, Yamasaki L, Jacks T (1998) Mutation of E2f-1 suppresses apoptosis and inappropriate S phase entry and extends survival of Rb-deficient mouse embryos. Mol Cell 2(3): 293-304 van den Heuvel S, and Dyson N J (2008) Conserved functions of the pRB and E2F families. Nat Rev Mol Cell Biol 9(9): 713-724

Wang, J., Guo, K., Wills, K. N., and Walsh, K. (1997). Rb functions to inhibit apoptosis during myocyte differentiation. Cancer Res 57, 351-354.

Weinberg, R. A. (1995). The retinoblastoma protein and cell cycle control. Cell 81, 323-330.

Wikonkal, N. M., Remenyik, E., Knezevic, D., Zhang, W., Liu, M., Zhao, H., Berton, T. R., Johnson, D. G., and Brash, D. E. (2003). Inactivating E2F-1 reverts apoptosis resistance and cancer sensitivity in Trp53-deficient mice. Nat Cell Biol 5, 655-660.

Yamasaki L, Bronson R, Williams B O, Dyson N J, Harlow E, Jacks T (1998) Loss of E2F-1 reduces tumorigenesis and extends the lifespan of Rb1(+/−) mice. Nat Genet. 18(4): 360-364

Zamanian, M., and La Thangue, N. B. (1992). Adenovirus E1a prevents the retinoblastoma gene product from repressing the activity of a cellular transcription factor. EMBO J. 11, 2603-2610.

The invention claimed is:

1. A method for the treatment of a cancer in an individual wherein said cancer expresses protein arginine N-methyltransferase 5 (PRMT5) and has increased methylation of the E2F-1 protein compared to noncancerous tissue comprising administering a therapeutically effective amount of an antisense molecule, an shRNA, an siRNA or a small molecule inhibitor of PRMT5 to an individual in need thereof, wherein said antisense molecule, said shRNA, said siRNA or said small molecule reduces expression or activity of said PRMT5 in said cancer thereby reducing or abolishing the ability of said PRMT5 to methylate said E2F-1 protein thereby promoting E2F-1-dependent apoptosis.

2. A method according to claim 1 wherein the method comprises administering a small molecule inhibitor of PRMT5.

3. A method according to claim 1 wherein the method comprises administering an antisense molecule.

4. A method according to claim 1 wherein the method comprises administering an shRNA.

5. A method according to claim 1 wherein the method comprises administering an siRNA.

* * * * *